(12) United States Patent
Adair et al.

(10) Patent No.: US 12,398,113 B2
(45) Date of Patent: Aug. 26, 2025

(54) METHODS FOR CONVERTING CBD, CBDA AND ANALOGS THEREOF INTO $\Delta^8$-THC, $\Delta^8$-THCA AND ANALOGS THEREOF

(71) Applicant: Canopy Growth Corporation, Smiths Falls (CA)

(72) Inventors: Christopher Adair, Smiths Falls (CA); Roger Gallant, Smiths Falls (CA); Ben Geiling, Smiths Falls (CA); Mohammadmehdi Haghdoost Manjili, Smiths Falls (CA)

(73) Assignee: Canopy Growth Corporation, Smiths Falls (CA)

( * ) Notice: Subject to any disclaimer, the term of this patent is extended or adjusted under 35 U.S.C. 154(b) by 923 days.

(21) Appl. No.: 17/644,690

(22) Filed: Dec. 16, 2021

(65) Prior Publication Data

US 2022/0106283 A1   Apr. 7, 2022

Related U.S. Application Data

(63) Continuation-in-part of application No. 17/596,364, filed as application No. PCT/CA2020/050804 on Jun. 11, 2020.

(60) Provisional application No. 62/860,097, filed on Jun. 11, 2019.

(51) Int. Cl.
*C07D 311/78* (2006.01)
*B01J 29/40* (2006.01)
*C07D 311/80* (2006.01)

(52) U.S. Cl.
CPC .............. *C07D 311/78* (2013.01); *B01J 29/40* (2013.01); *C07D 311/80* (2013.01)

(58) Field of Classification Search
CPC .................................................. C07D 311/78
See application file for complete search history.

(56) References Cited

U.S. PATENT DOCUMENTS

| | | |
|---|---|---|
| 7,321,047 B2 | 1/2008 | Field et al. |
| 7,399,872 B2 | 7/2008 | Webster et al. |
| 7,674,922 B2 | 3/2010 | Burdick et al. |
| 7,923,558 B2 | 4/2011 | Arslantas et al. |
| 8,324,408 B2 | 12/2012 | Erler et al. |
| 9,744,151 B2 | 8/2017 | Gutman et al. |
| 10,059,683 B2 | 8/2018 | Dialer et al. |
| 2004/0143126 A1* | 7/2004 | Webster ............... C07D 311/80 549/390 |
| 2004/0248970 A1 | 12/2004 | Webster et al. |
| 2007/0287843 A1 | 12/2007 | Cabaj et al. |
| 2008/0221339 A1 | 9/2008 | Webster et al. |
| 2010/0069651 A1 | 3/2010 | Burdick et al. |
| 2010/0210860 A1 | 8/2010 | Erler et al. |
| 2017/0226077 A1 | 8/2017 | Bach |
| 2018/0104214 A1 | 4/2018 | Raichman |
| 2018/0263283 A1 | 9/2018 | Popplewell et al. |
| 2019/0328040 A1 | 10/2019 | Turbi |
| 2020/0223814 A1 | 7/2020 | Nivorozhkin |

FOREIGN PATENT DOCUMENTS

| | | | |
|---|---|---|---|
| AU | 2012201041 A1 | 3/2012 | |
| CA | 3061143 A1 | 5/2020 | |
| WO | WO 2002/070506 A2 | 9/2002 | |
| WO | WO 2006/136273 A1 | 12/2006 | |
| WO | WO 2007/041167 A2 | 4/2007 | |
| WO | WO 2016/050245 A1 | 4/2016 | |
| WO | WO 2017/205692 A1 | 11/2017 | |
| WO | WO 2019/173582 A1 | 9/2019 | |
| WO | WO 2020/146907 A1 | 7/2020 | |
| WO | WO-2021207605 A1 * | 10/2021 | ............. B01J 20/12 |

OTHER PUBLICATIONS

Uliss et al. Tetrahedron 1978, 34, 1885-1888 (Year: 1978).*
Tius et al. Tetrahedron 1992, 48, 9173-86 (Year: 1992).*
Drake et al. J. Med. Chem. 1998, 4, 3596-3608 (Year: 1998).*
Huang et al. Tetrahedron 2007, 63, 1014-1021 (Year: 2007).*
Hanus et al. Org. Biomol. Chem. 2005, 3, 1116-1123 (Year: 2005).*
Adams, et al., "Structure of Cannabidiol. VI. Isomerization of Cannabidiol to Tetrahydrocannabinol, a Physiologically Active Product. Conversion of Cannabidiol to Cannabinol", *Journal of the American Chemical Society*, 1940, 62(9): 2402-2405.
Adams et al., "Structure of Cannabidiol. XII. Isomerization to Tetrahydrocannabinols", *Journal of the American Chemical Society*, 1941, 63(8): 2209-2213.
Abrahamov et al., "An efficient new cannabinoid antiemetic in pediatric oncology", *Life Sciences*, 1995, 56(23/24): 2097-2102.
Gaoni, et.al., "Hashish-VII : The isomerization of cannabidiol to tetrahydrocannabinols", *Tetrahedron*, 1966, 22(4): 1481-1488.
Garcia, et al., "Thermal isomerization of cannabinoid analogues", *Journal of the American Chemical Society*, 2009, 131(46): 16640-16641.
Giorgi et al., "Biomimetic Cannabinoid Synthesis Revisited: Batch and Flow All-Catalytic Synthesis of (±)-ortho-Tetrahydrocannabinols and Analogues from Natural Feedstocks", *European Journal of Organic Chemistry*, 2018, 2018(11): 1307-1311.
Inayama et al., "The Oxidation of $\Delta^1$ and $\Delta^6$-Tetrahydrocannabinol with Selenium Dioxide", *Chemical and Pharmaceutical Bulletin*, 1974, 22(7): 1519-1525.

(Continued)

*Primary Examiner* — Amanda L. Aguirre
(74) *Attorney, Agent, or Firm* — Knobbe, Martens, Olson & Bear, LLP

(57) ABSTRACT

Disclosed herein are methods for converting cannabidiol, cannabidiolic acid and analogs thereof into $\Delta^8$-tetrahydrocannabinol, $\Delta^8$-tetrahydrocannabinolic acid and analogs thereof. In particular, there is provided a method for converting a compound of Formula (I) as defined herein into a compound of Formula (II) as defined herein, the method comprising heating the compound of Formula (I) and a Lewis acidic heterogeneous reagent in an aprotic-solvent system to provide a compound of Formula (II), wherein the Lewis-acidic heterogeneous reagent is acidic alumina.

20 Claims, 13 Drawing Sheets

(56) References Cited

OTHER PUBLICATIONS

Handrick et al., "Hashish. Synthesis of (±)-$\Delta^1$- and $\Delta^6$-3,4-cis-Cannabidiols and Their Isomerization by Acid Catalysis", *Journal of Organic Chemistry*, 1977, 42(15): 2563-2568.

Hively et al., "Isolation of trans-$\Delta^6$-tetrahydrocannabinol from Marijuana", *Journal of the American Chemical Society*, 1966, 88(8): 1832-1833.

Holler et al., "Isomerization of delta-9-THC to delta-8-THC when tested as trifluoroacetyl-, pentafluoropropionyl-, or heptafluorobutyryl-derivatives", *Journal of Mass Spectrometry*, 2008, 43(5): 674-679.

Hollister et al., "Delta-8- and delta-9-tetrahydrocannabinol; Comparison in man by oral and intravenous administration", *Clinical Pharmacology and Therapeutics*, 1973, 14(3): 353-357.

Huffman, et al., "Stereoselective synthesis of the epimeric $\Delta7$-tetrahydrocannabinols", *Tetrahedron*, 1995, 51(4): 1017-1032.

Huffman, et al., "Synthesis of 5', 11-dihydroxy-$\Delta8$-tetrahydrocannabinol", *Tetrahedron*, 1997, 53(39): 13295-13306.

Matsuzaki, et al., "Application of Hammett indicators to estimating coverages of acid sites of silica-alumina by nitrogen, ethylene, water, ethyl alcohol, pyridine and n-butylamine." *Journal of the Research Institute for Catalysis Hokkaido University*, 1969, 17(1): 46-53.

Mechoulam et al., "Hashish. XII. Stereoelectronic factor in the chloranil dehydrogenation of cannabinoids. Total synthesis of dl-cannabichromene", *J. Am. Chem. Soc.*, 1968, 90(9): 2418-2420.

Price et al., "Solvent Effects in the Base-Catalyzed Isomerization of Allyl to Propenyl Ethers", *Journal of the American Chemical Society*, 1961, 83(7): 1773.

Schafroth et al., "Synthesis of phytocannabinoids." *Phytocannabinoids*, 2018: 35-59.

Srebnik et al., "Base-catalysed double-bond isomerizations of cannabinoids: structural and stereochemical aspects", *Chem. Soc., Perkin Trans. 1*, 1984, 2881-2886.

Sun, et al., "A novel methodology for the synthesis of 1-desoxy-$\Delta8$-tetrahydrocannabinol (THC) analogues", *Tetrahedron Letters*, 2004, 45(3): 615-617.

Tius, Marcus, "Stereospecific cannabinoid synthesis: The application of new techniques to a classical problem", *Studies in Natural Products Chemistry*, 1996, 19: 185-244.

Uliss, et al., "Hashish: Synthesis of dl-$\delta$1,6-cis-tetrahydrocannabinol (THC)", *Tetrahedron Letters*, 1975, 16(49): 4369-4372.

Uliss, et al., "The conversion of 3,4-cis- to 3,4-trans-cannabinoids", *Tetrahedron*, 1978, 34(13): 1885-1888.

Valter, et al., "2.4: Synthetic Cannabinoids", *Designer Drugs Directory*, 1998: 99-100.

Veress et al., "Determination of the characteristic components in hashish and marijuana type drugs of abuse. II. Determination of cannabinoid acids by using decarboxylation and HPLC", *Magyar Kemiai Folyoirat*, 1989, 95(2): 59-65.

Yagen, et al., "Stereospecific cyclizations and isomerizations of cannabichromene and related cannabinoids". *Tetrahedron Letters*, 1969, 10(60): 5353-5356.

Zwackelmann, "Cannabidiol to THC-simple, Hive Methods Discourse", No. 479001, Dec. 25, 2003.

Communication pursuant to Rule 164(1) EPC dated Jun. 15, 2023, in Respect of European Application No. 20822000.4.

* cited by examiner

METHODS FOR CONVERTING CBD, CBDA AND ANALOGS THEREOF INTO $\Delta^8$-THC, $\Delta^8$-THCA AND ANALOGS THEREOF

CROSS-REFERENCE TO RELATED APPLICATIONS

This application is a continuation-in-part of U.S. patent application Ser. No. 17/596,364 filed on Dec. 8, 2021, which is a national stage filing under 35 U.S.C. 371 of International Application No. PCT/CA2020/050804, which, in turn, claims the benefit of priority to U.S. Provisional Patent Application Ser. No. 62/860,097 filed on Jun. 11, 2019, each of which are hereby incorporated by reference in their entirety.

TECHNICAL FIELD

The present disclosure generally relates to methods for isomerizing cannabinoids. In particular, the present disclosure relates to methods for converting cannabidiol, cannabidiolic acid and analogs thereof into $\Delta^8$-tetrahydrocannabinol, $\Delta^8$-tetrahydrocannabinolic acid and analogs thereof.

BACKGROUND

Since the discovery of specific receptors for cannabinoids in mammalian brain and peripheral tissues, cannabinoids have attracted renewed interest for medicinal and recreational applications. In particular, $\Delta^9$-tetrahydrocannabinol ($\Delta^9$-THC) has been the focus of numerous studies. For example, Dronabinol—a synthetic form of $\Delta^9$-THC—is currently being investigated for a wide variety of therapies relating to glaucoma, arthritis, chronic pain, cancer, multiple sclerosis, and other diseases.

$\Delta^8$-tetrahydrocannabinol ($\Delta^8$-THC) is a regioisomer of $\Delta^9$-THC and, relative to $\Delta^9$-THC, $\Delta^8$-THC has received relatively little attention. Notably, the cannabinoid receptor binding affinity for $\Delta^8$-THC is similar to that of $\Delta^9$-THC, but $\Delta^8$-THC is reported to be approximately 50% less potent in terms of psychoactivity. Hence, methods for forming $\Delta^8$-THC selectively are attractive, but there is a paucity of information in this respect. There is also a paucity of information on methods that provide mixtures of $\Delta^8$-THC and $\Delta^9$-THC in which $\Delta^8$-THC is the major product. Instead, the vast majority of methods for preparing THC are aimed at forming $\Delta^9$-THC selectively, and little is known about the therapeutic and/or recreational utility of mixtures of $\Delta^8$-THC and $\Delta^9$-THC in which $\Delta^8$-THC is more than a minor component.

$\Delta^8$-THC and $\Delta^9$-THC can both be prepared from cannabidiol (CBD). However, known methods for converting CBD to $\Delta^8$-THC and/or $\Delta^9$-THC typically employ chemicals that are dangerous, and/or toxic. Moreover, such methods typically rely on protocols that are generally considered hazardous and/or not suitable for industrial scale reactions (e.g. reagent-addition, quenching, and/or work-up steps that are highly exothermic). Several known methods for converting CBD to $\Delta^8$-THC and/or $\Delta^9$-THC also require special care to eliminate oxygen and moisture from the reaction vessel for optimal reactivity and safety. Accordingly, improved methods of converting CBD into $\Delta^8$-THC, including acidic forms and analogs thereof, are desirable.

SUMMARY

The present disclosure provides improved methods of converting cannabidiol (CBD) into primarily $\Delta^8$-tetrahydrocannabinol ($\Delta^8$-THC) or mixtures of $\Delta^8$-THC and $\Delta^9$-tetrahydrocannabinol ($\Delta^9$-THC) having $\Delta^8$-THC:$\Delta^9$-THC ratios of greater than 1.0:1.0. The methods herein may be performed with neutral or acidic forms of CBD, as well as analogs of such compounds as described herein.

In an embodiment, the present disclosure relates to methods for converting a compound of Formula (I) into a compound of Formula (II), where the compounds of Formula (I) and Formula (II) are as follows:

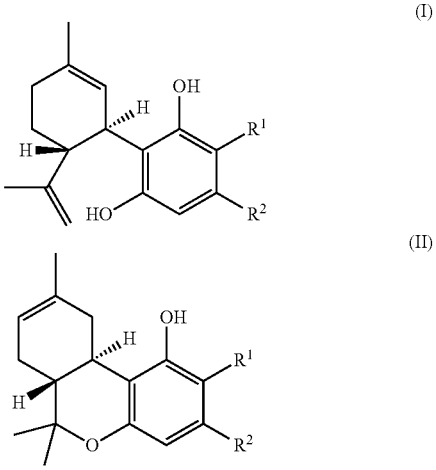

wherein $R^1$ is hydrogen or COOH, and $R^2$ is hydrogen, $C_1$-$C_{12}$ alkyl, $C_2$-$C_{12}$ alkenyl, $C_2$-$C_{12}$ alkynyl, (OCH$_2$CH$_2$)$_{0-6}$O($C_1$-$C_8$ alkyl), ($C_0$-$C_4$ alkyl)-NR$^{2a}$R$^{2b}$, ($C_0$-$C_4$ alkyl)-aryl, ($C_0$-$C_4$ alkyl)-heteroaryl, ($C_0$-$C_4$ alkyl)-cycloalkyl, or ($C_0$-$C_4$ alkyl)-heterocycloalkyl, wherein R$^{2a}$R$^{2b}$ are each independently hydrogen or $C_1$-$C_6$ alkyl.

In select embodiments of the methods of the present disclosure, $R^2$ is $C_3H_7$, $C_5H_{11}$ or $C_7H_{15}$. In certain embodiments, the compound of Formula (I) is CBD and the compound of Formula (II) is $\Delta^8$-THC. In certain embodiments, the compound of Formula (I) is cannabidiolic acid (CBDA) and the compound of Formula (II) is $\Delta^8$-tetrahydrocannabinolic acid ($\Delta^8$-THCA). In certain embodiments as described herein, the compound of Formula (I) is other than CBD and the compound of Formula (II) is other than $\Delta^8$-THC.

In select embodiments of the methods disclosed herein, the resulting compound of Formula (II) is a component of a composition that further comprises a compound of Formula (III)

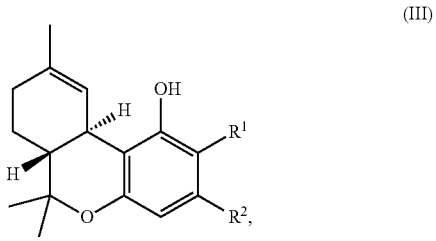

wherein the composition has a compound of Formula (II): compound of Formula (III) ratio that is greater than 1.0:1.0. As used herein, the expression "$\Delta^8$:$\Delta^9$ ratio" may be used interchangeably and as a short form for "compound of Formula (II):compound of Formula (III) ratio". As used herein, the expression "$\Delta^8$ regioisomer" is intended to refer to compounds of Formula (II) and "$\Delta^9$ regioisomer" is intended to refer to compounds of Formula (III).

The methods of the present disclosure are suitable for use at industrial scale in that they do not require: (i) complicated and/or dangerous reagent-addition, quenching, and/or work-up steps; and (ii) dangerous and/or toxic solvents and/or reagents. Importantly, embodiments of the methods of the present disclosure provide access to compositions with wide-ranging $\Delta^8:\Delta^9$ ratios as evidenced by the wide-ranging $\Delta^8$-THC:$\Delta^9$-THC ratios disclosed herein. Because the $\Delta^8$-THC:$\Delta^9$-THC ratios disclosed herein can be correlated to particular reaction conditions and reagents, the methods of the present disclosure can be tuned towards particular $\Delta^8:\Delta^9$ ratio (e.g. $\Delta^8$-THC/$\Delta^9$-THC ratio) selectivity outcomes.

The present disclosure asserts that the ability to form primarily $\Delta^8$ regioisomers (e.g. $\Delta^8$-THC) and/or compositions having various $\Delta^8:\Delta^9$ ratios (e.g. $\Delta^8$-THC:$\Delta^9$-THC ratios) which are greater than 1.0:1.0 as demonstrated herein is associated with the utilization of Lewis-acidic heterogeneous reagents. Results disclosed herein indicate that slight changes to reaction conditions involving Lewis-acidic heterogeneous reagents can be leveraged to provide particular $\Delta^8:\Delta^9$ ratio (e.g. $\Delta^8$-THC/$\Delta^9$-THC ratio) selectivities. The utilization of Lewis-acidic heterogeneous reagents for the present transformations also appears to be compatible with the use of class III solvents (or neat reaction conditions) which may obviate the need for the dangerous and/or hazardous solvents that are typical of the prior art. The utilization of Lewis-acidic heterogeneous reagents may also allow product mixtures to be isolated by simple solid/liquid separations (e.g. filtration and/or decantation). As such, the utilization of Lewis-acidic heterogeneous reagents appears to underlie one more of the advantages of the present disclosure.

In select embodiments, the present disclosure relates to a method for converting a compound of Formula (I) as defined herein into a compound of Formula (II) as defined herein, the method comprising contacting a compound of Formula (I) as defined herein with a Lewis-acidic heterogeneous reagent, in a protic-solvent system, an aprotic-solvent system or under neat conditions, to provide a compound of Formula (II) as defined herein, wherein the Lewis-acidic heterogeneous reagent is an ion-exchange resin, a microporous silicate, a mesoporous silicate, a phyllosilicate, or a combination thereof.

In select embodiments, the present disclosure relates to a method for converting CBD into a composition comprising $\Delta^8$-THC and $\Delta^9$-THC, in which the composition has a $\Delta^8$-THC:$\Delta^9$-THC ratio that is greater than 1.0:1.0. In such embodiments, the method may comprise contacting the CBD with a Lewis-acidic heterogeneous reagent under reaction conditions comprising: (i) an aprotic-solvent system; (ii) a reaction temperature that is greater than a threshold reaction temperature for the Lewis-acidic heterogeneous reagent and the aprotic-solvent system; and (iii) a reaction time that is greater than a threshold reaction time for the Lewis-acidic heterogeneous reagent, the aprotic-solvent system, and the reaction temperature.

In select embodiments, the present disclosure relates to a method for converting CBD into primarily $\Delta^8$-THC. In such embodiments, the method may comprise contacting the CBD with a Lewis-acidic heterogeneous reagent under reaction conditions comprising: (i) an aprotic-solvent system; (ii) a reaction temperature that is greater than a threshold reaction temperature for the Lewis-acidic heterogeneous reagent and the aprotic-solvent system; and (iii) a reaction time that is greater than a threshold reaction time for the Lewis-acidic heterogeneous reagent, the aprotic-solvent system, and the reaction temperature.

In select embodiments, the present disclosure relates to a method for converting CBD into a composition comprising $\Delta^8$-THC and $\Delta^9$-THC, in which the composition has a $\Delta^8$-THC:$\Delta^9$-THC ratio that is greater than 1.0:1.0. In such embodiments, the method may comprise contacting the CBD with a Lewis-acidic heterogeneous reagent under neat reaction conditions comprising: (i) a reaction temperature that is greater than a threshold reaction temperature for the Lewis-acidic heterogeneous reagent; and (ii) a reaction time that is greater than a threshold reaction time for the Lewis-acidic heterogeneous reagent and the reaction temperature.

In select embodiments, the present disclosure relates to a method for converting CBD into primarily $\Delta^8$-THC. In such embodiments, the method may comprise contacting the CBD with a Lewis-acidic heterogeneous reagent under neat reaction conditions comprising: (i) a reaction temperature that is greater than a threshold reaction temperature for the Lewis-acidic heterogeneous reagent; and (ii) a reaction time that is greater than a threshold reaction time for the Lewis-acidic heterogeneous reagent and the reaction temperature.

In select embodiments, the present disclosure relates to a method for converting CBD into a composition comprising $\Delta^8$-THC and $\Delta^9$-THC, in which the composition has a $\Delta^8$-THC:$\Delta^9$-THC ratio that is greater than 1.0:1.0. In such embodiments, the method may comprise contacting the CBD with a Lewis-acidic heterogeneous reagent under reaction conditions comprising: (i) a protic-solvent system; (ii) a reaction temperature that is greater than a threshold reaction temperature for the Lewis-acidic heterogeneous reagent and the protic-solvent system; and (iii) a reaction time that is greater than a threshold reaction time for the Lewis-acidic heterogeneous reagent, the protic-solvent system, and the reaction temperature.

In select embodiments, the present disclosure relates to a method for converting CBD into primarily $\Delta^8$-THC. In such embodiments, the method may comprise contacting the CBD with a Lewis-acidic heterogeneous reagent under reaction conditions comprising: (i) a protic-solvent system; (ii) a reaction temperature that is greater than a threshold reaction temperature for the Lewis-acidic heterogeneous reagent and the protic-solvent system; and (iii) a reaction time that is greater than a threshold reaction time for the Lewis-acidic heterogeneous reagent, the protic-solvent system, and the reaction temperature.

In select embodiments, the present disclosure relates to a method for converting CBD into primarily $\Delta^8$-THC. In such embodiments, the method may comprise contacting the CBD with an ion-exchange resin under reaction conditions comprising: (i) a class III solvent; (ii) a reaction temperature that is greater than about 60° C.; and (iii) a reaction time that is greater than about 60 minutes.

In select embodiments, the present disclosure relates to a method for converting CBD into a composition comprising $\Delta^8$-THC and $\Delta^9$-THC, in which the composition has a $\Delta^8$-THC:$\Delta^9$-THC ratio that is greater than 1.0:1.0. In such embodiments, the method may comprise contacting the CBD with an aluminosilicate-based reagent under reaction conditions comprising: (i) a class III solvent; (ii) a reaction temperature that is greater than about 70° C.; and (iii) a reaction time that is greater than about 60 minutes.

In select embodiments, the present disclosure relates to a method for converting a compound of Formula (I) as defined herein into a compound of Formula (II) as defined herein, the method comprising heating a compound of Formula (I) as defined herein and a Lewis-acidic heterogeneous reagent in an aprotic-solvent system, to provide a compound of Formula (II) as defined herein, wherein the Lewis-acidic heterogeneous reagent is acidic alumina.

In select embodiments, the present disclosure relates to a method for converting cannabidiol (CBD) into $\Delta^8$-tetrahydrocannabinol ($\Delta^8$-THC), the method comprising heating CBD and a Lewis-acidic heterogeneous reagent in an aprotic-solvent system, wherein the Lewis-acidic heterogeneous reagent is acidic alumina.

In select embodiments, the present disclosure relates to a method for converting cannabidiol (CBD) into $\Delta^8$-tetrahydrocannabinol ($\Delta^8$-THC), the method comprising heating CBD and a Lewis-acidic heterogeneous reagent in an aprotic-solvent system at a temperature in a range from about 80° C. to about 110° C., and wherein the Lewis-acidic heterogeneous reagent is acidic alumina and is in an amount of between about 1 to about 100 molar equivalents with respect to CBD.

In select embodiments, the present disclosure relates to a method for converting a compound of Formula (I) as defined herein into a compound of Formula (II) as defined herein, the method comprising contacting a compound of Formula (I) as defined herein with a Lewis-acidic heterogeneous reagent, optionally in an aprotic-solvent system, to provide a compound of Formula (II) as defined herein, wherein the Lewis-acidic heterogeneous reagent is an ion-exchange resin, a microporous silicate, a mesoporous silicate, a phyllosilicate, or a combination thereof; and wherein the compound of Formula (I) is other than cannabidiol (CBD) and the compound of Formula (II) is other than $\Delta^8$-tetrahydrocannabinol ($\Delta^8$-THC).

Other aspects and features of the present disclosure will become apparent to those ordinarily skilled in the art upon review of the following description of specific embodiments.

DETAILED DESCRIPTION

Figure 1:
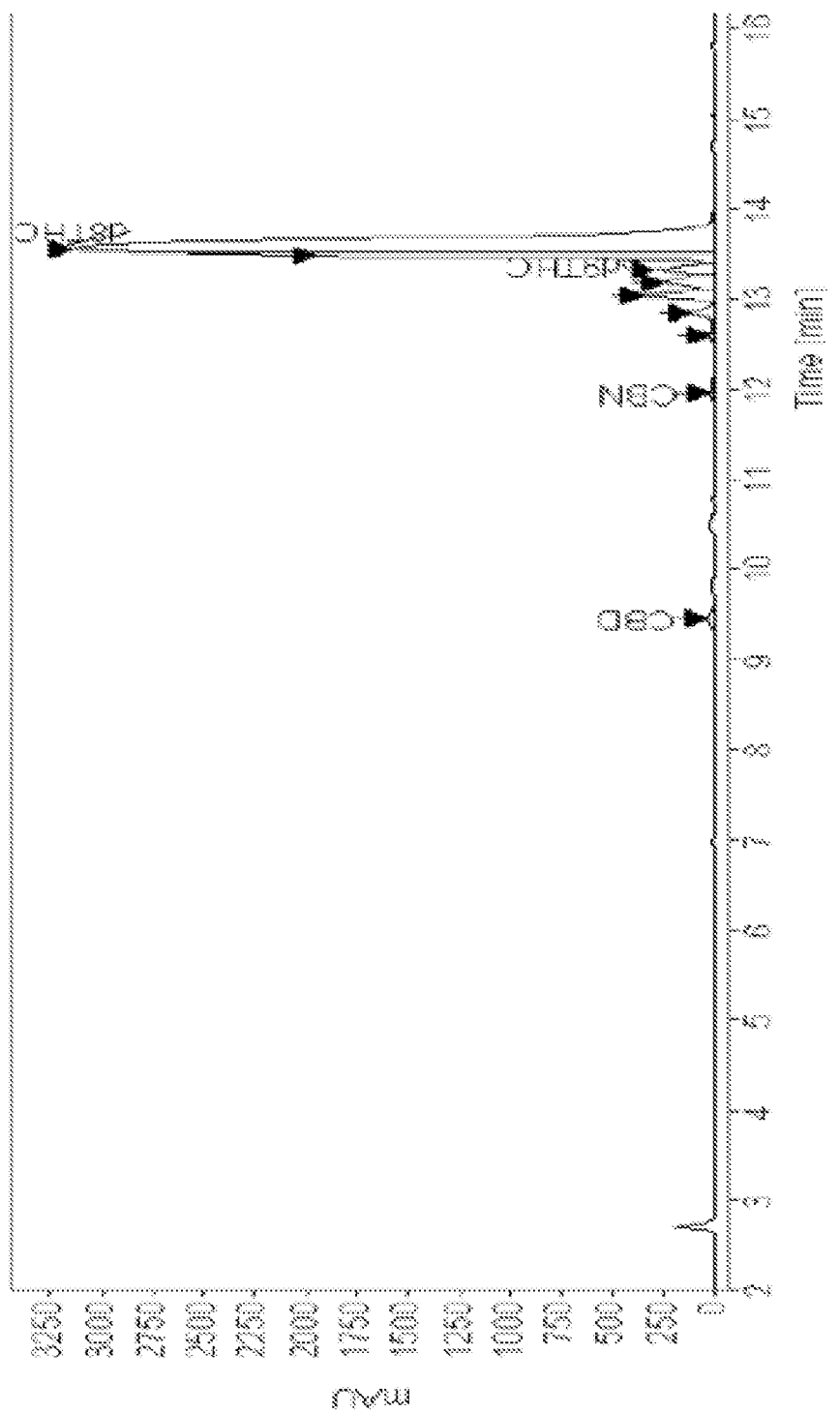
FIG. 1 shows a high-performance liquid chromatogram for EXAMPLE 1.

As noted above, the present disclosure provides improved methods for converting a first cannabinoid into primarily a second cannabinoid or mixtures of a second cannabinoid and a third cannabinoid in which the second cannabinoid:third cannabinoid ratio is greater than 1.0:1.0. The methods of the present disclosure are suitable for use at industrial scale in that they do not require: (i) complicated and/or dangerous reagent addition, quenching, and/or work-up steps; and (ii) dangerous and/or toxic solvents and/or reagents. Importantly, the methods of the present disclosure provide access to compositions having wide-ranging second cannabinoid:third cannabinoid ratios as evidenced by the wide-ranging second cannabinoid/third cannabinoid selectivity disclosed herein. For example, in select embodiments, a first set of reaction conditions disclosed herein provides a second cannabinoid:third cannabinoid ratio of about 1.5:1.0, and a second set of reaction conditions disclosed herein provides a second cannabinoid:third cannabinoid ratio of about 19.2:1.0. Because the reagents and reaction conditions disclosed herein can be correlated to particular second cannabinoid:third cannabinoid ratios, the methods of the present disclosure may be tuned towards particular second cannabinoid/third cannabinoid selectivity outcomes. While there may be little information available in the current research literature on pharmacokinetic interactions between mixtures of isomeric cannabinoids having defined ratios, the present disclosure asserts that access to an array of compositions of wide-ranging isomeric ratios is desirable in both medicinal and recreational contexts. Moreover, the present disclosure asserts that access to an array of compositions of varying isomeric ratios is desirable to synthetic chemists.

Without being bound to any particular theory, the present disclosure asserts that the ability to convert a first cannabinoid into primarily a second cannabinoid that is an isomer of the first cannabinoid or into a composition comprising isomeric cannabinoids in various ratios as demonstrated herein is associated with the utilization of Lewis-acidic heterogeneous reagents. Results disclosed herein indicate that slight changes to reaction conditions involving Lewis-acidic heterogeneous reagents can be leveraged to provide particular isomeric selectivities. The utilization of Lewis-acidic heterogeneous reagents also appears to be compatible with the use of class III solvents (or neat reaction conditions) which may obviate the need for the dangerous and/or hazardous solvents that are typical of the prior art. The utilization of Lewis-acidic heterogeneous reagents may also allow product mixtures to be isolated by simple solid/liquid separations (e.g. filtration and/or decantation). As such, the utilization of Lewis-acidic heterogeneous reagents appears to underlie one or more of the advantages of the present disclosure.

In select embodiments, the present disclosure relates to methods for converting a compound of Formula (I) into a compound of Formula (II), where the compounds of Formula (I) and Formula (II) are as follows:

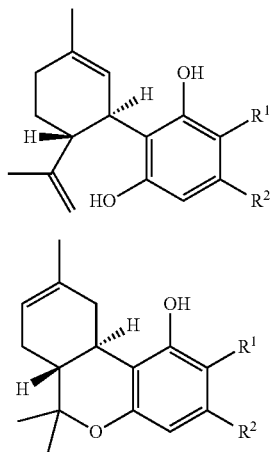

(I)

(II)

wherein:
R¹ is hydrogen or COOH, and
R² is hydrogen, $C_1$-$C_{12}$ alkyl, $C_2$-$C_{12}$ alkenyl, $C_2$-$C_{12}$ alkynyl, $(OCH_2CH_2)_{0-6}O(C_1$-$C_8$ alkyl), $(C_0$-$C_4$ alkyl)-$NR^{2a}R^{2b}$, $(C_0$-$C_4$ alkyl)-aryl, $(C_0$-$C_4$ alkyl)-heteroaryl, $(C_0$-$C_4$ alkyl)-cycloalkyl, or $(C_0$-$C_4$ alkyl)-heterocycloalkyl, wherein $R^{2a}R^{2b}$ are each independently hydrogen or $C_1$-$C_6$ alkyl. As used herein, the term "analog" is intended to refer to any compound of Formula (I), (II) or (III) herein in which R² is other than $C_5H_{11}$.

In an embodiment of the methods disclosed herein, R¹ is hydrogen. In other embodiments, R¹ is COOH. In an embodiment of the methods disclosed herein, R² is $C_3H_7$, $C_5H_{11}$ or $C_7H_{15}$. In a particular embodiment, R² is $C_3H_7$. In a particular embodiment, R² is $C_5H_{11}$. In a particular embodiment, R² is or $C_7H_{15}$. In some embodiments, R² is other than $C_5H_{11}$ when R¹ is hydrogen. In some embodiments, R² is other than hydrogen.

In an embodiment of the methods disclosed herein, the compound of Formula (I) is cannabidiol (CBD) and the compound of Formula (II) is Δ⁸-tetrahydrocannabinol (Δ⁸-THC). In such compounds, R¹ is hydrogen and R² is $C_5H_{11}$. In other select embodiments, the compound of Formula (I) is other than CBD and the compound of Formula (II) is other than Δ⁸-THC.

In an embodiment of the methods disclosed herein, the compound of Formula (I) is cannabidiolic acid (CBDA) and the compound of Formula (II) is Δ⁸-tetrahydrocannabinolic acid (Δ⁸-THCA). In such compounds, R¹ is COOH and R² is $C_5H_{11}$.

In an embodiment of the methods disclosed herein, the compound of Formula (I) is cannabidivarin (CBDV) and the compound of Formula (II) is Δ⁸-tetrahydrocannabivarin (Δ⁸-THCV). In such compounds, R¹ is hydrogen and R² is $C_3H_7$.

In an embodiment of the methods disclosed herein, the compound of Formula (I) is cannabidiphorol (CBDP) and the compound of Formula (II) is Δ⁸-tetrahydrocannabiphorol (Δ⁸-THCP). In such compounds, R¹ is hydrogen and R² is $C_7H_{15}$.

The compounds of Formula (I) for use in the methods disclosed herein may be obtained from any source or origin. In an embodiment, the compounds of Formula (I) are from a natural source (e.g. a plant material, such as a cannabis plant material). In an embodiment, the compounds of Formula (I) may be synthetic or semi-synthetic. By "synthetic"

it is meant that the compound is human-made, rather than produced by nature. By "semi-synthetic" it is meant to refer to a compound or substance that is obtained from a natural source (e.g. plant material) and subsequently modified or derivatized in one or more different ways. In an embodiment, the compound of Formula (I) is a component of a distillate, an isolate, a concentrate, an extract, or a combination thereof. In an embodiment, the compound of Formula (I) is a component of a cannabinoid isolate, a cannabis concentrate, a cannabis extract (e.g. cannabis oil), or any combination thereof. In an embodiment, the compound of Formula (I) is a pure compound.

In select embodiments of the methods disclosed herein, the resulting compound of Formula (II) is a component of a composition that further comprises a compound of Formula (III)

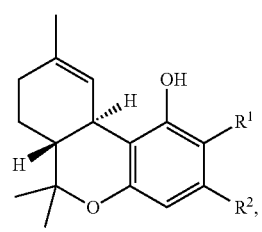

(III)

wherein R¹ and R² are as defined elsewhere herein and wherein the composition has a compound of Formula (II): compound of Formula (III) ratio that is greater than 1.0:1.0.

As used herein, the expression "Δ⁸:Δ⁹ ratio" may be used interchangeably and as a short form for "compound of Formula (II):compound of Formula (III) ratio". As shown in the structural formulae herein, the compound of Formula (II) is a Δ⁸ regioisomer and the compound of Formula (III) is a Δ⁹ regioisomer.

In an embodiment of the methods disclosed herein, the compositions have a Δ⁸:Δ⁹ ratio on a weight/weight basis (w/w) of: (i) greater than about 2.0:1.0; (ii) greater than about 3.0:1.0; (iii) greater than about 5.0:1.0; (iv) greater than about 10.0:1.0; (v) greater than about 15.0:1.0; (vi) greater than about 20.0:1.0; (vii) greater than about 50.0:1.0; or (viii) greater than about 100.0:1.0. In an embodiment, the Δ⁸:Δ⁹ ratio (w/w) is between about 100:1 and about 1.5:1, more particularly between about 50:1 and about 2:1, and more particularly still between about 25:1 and about 5:1. In an embodiment, the Δ⁸:Δ⁹ ratio (w/w) is about 50:1, about 45:1, about 40:1, about 35:1, about 30:1, about 25:1, about 24:1, about 23:1, about 22:1, about 21:1, about 20:1, about 19:1, about 18:1, about 17:1, about 16:1, about 15:1, about 14:1, about 13:1, about 12:1, about 11:1, about 10:1, about 9:1, about 8:1, about 7:1, about 6:1, about 5:1, about 4:1, about 3:1, or about 2:1.

In select embodiments, the methods disclosed herein are performed in a protic-solvent system, an aprotic-solvent system or under neat conditions (i.e. without solvent). In a particular, embodiment, the methods disclosed herein are performed in an aprotic-solvent system, such as for example the aprotic-solvent systems as described herein. In a particular, embodiment, the methods disclosed herein are performed under neat conditions.

In an embodiment, the present disclosure thus relates to a method for converting a compound of Formula (I) as defined herein into a compound of Formula (II) as defined herein, the method comprising contacting a compound of Formula (I) as defined herein with a Lewis-acidic heterogeneous reagent, in a protic-solvent system, an aprotic-solvent system or under neat conditions, to provide a compound of Formula (II) as defined herein, wherein the Lewis-acidic heterogeneous reagent is an ion-exchange resin, a microporous silicate, a mesoporous silicate, a phyllosilicate, or a combination thereof.

In select embodiments, the present disclosure relates to a method for converting a compound of Formula (I) into a compound of Formula (II), the method comprising contacting the compound of Formula (I)

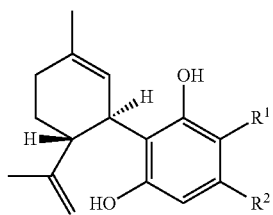

(I)

with a Lewis-acidic heterogeneous reagent, optionally in an aprotic-solvent system, to provide a compound of Formula (II)

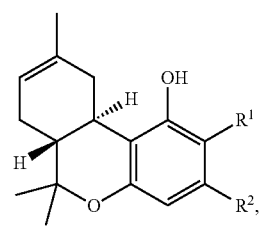

(II)

wherein $R^1$ is hydrogen or COOH, and $R^2$ is hydrogen, $C_1$-$C_{12}$ alkyl, $C_2$-$C_{12}$ alkenyl, $C_2$-$C_{12}$ alkynyl, (OCH$_2$CH$_2$)$_{0-6}$O($C_1$-$C_8$ alkyl), ($C_0$-$C_4$ alkyl)-NR$^{2a}$R$^{2b}$, ($C_0$-$C_4$ alkyl)-aryl, ($C_0$-$C_4$ alkyl)-heteroaryl, ($C_0$-$C_4$ alkyl)-cycloalkyl, or ($C_0$-$C_4$ alkyl)-heterocycloalkyl, wherein $R^{2a}R^{2b}$ are each independently hydrogen or $C_1$-$C_6$ alkyl.

In an embodiment of the preceding method for preparing a compound of Formula (II), contacting the compound of Formula (I) with a Lewis-acidic heterogeneous reagent is in an aprotic-solvent system such as those described herein. In another embodiment, contacting the compound of Formula (I) with a Lewis-acidic heterogeneous reagent is under neat conditions.

In an embodiment of the preceding method for preparing a compound of Formula (II), the Lewis-acidic heterogeneous reagent is any Lewis-acidic heterogeneous reagent as described herein or any combination thereof.

In a particular embodiment, the Lewis-acidic heterogeneous reagent is acidic alumina. In certain embodiments of such methods, $R^1$ is hydrogen. In certain embodiments of such methods, $R^2$ is $C_3H_7$, $C_5H_{11}$ or $C_7H_{15}$. In a particular embodiment, $R^2$ is $C_3H_7$. In a particular embodiment, $R^2$ is $C_5H_{11}$. In a particular embodiment, $R^2$ is or $C_7H_{15}$. In certain embodiments of such methods, the compound of Formula (I) is CBD and the compound of Formula (II) is $\Delta^8$-THC. In certain embodiments of such methods, the compound of Formula (I) is CBDA and the compound of Formula (II) is $\Delta^8$-THCA. In certain embodiments of such methods, the compound of Formula (I) is CBDV and the compound of Formula (II) is $\Delta^8$-THCV. In certain embodiments of such methods, the compound of Formula (I) is CBDP and the compound of Formula (II) is $\Delta^8$-THCP.

In a particular embodiment, the Lewis-acidic heterogeneous reagent is an ion-exchange resin, a microporous silicate, a mesoporous silicate, a phyllosilicate, or any combination thereof. In an embodiment, when the Lewis-acidic heterogeneous reagent is an ion-exchange resin, it is other than Amberlyst-15 or Nafion-SAC-13. In an embodiment, when the Lewis-acidic heterogeneous reagent is a microporous silicate, it is other than Zeolite Y, Zeolite Beta, or SAPO-11. In an embodiment of any such methods in which the Lewis-acidic heterogeneous reagent is an ion-exchange resin, a microporous silicate, a mesoporous silicate, a phyllosilicate, or any combination thereof, the compound of Formula (I) is other than CBD and the compound of Formula (II) is other than $\Delta^8$-THC.

As described above, select embodiments of the methods of the present disclosure are for converting a compound of Formula (I) into a composition comprising a compound of Formula (II) and a compound of Formula (III), wherein the composition has a compound of Formula (II):compound of Formula (III) ratio that is greater than 1.0:1.0. In an embodiment, the compound of Formula (II):compound of Formula (III) ratio is any of the $\Delta^8$:$\Delta^9$ ratios disclosed herein.

In select embodiments, the present disclosure relates to a method for converting CBD into a composition comprising $\Delta^8$-THC and $\Delta^9$-THC, wherein the composition has a $\Delta^8$-THC:$\Delta^9$-THC ratio that is greater than 1.0:1.0, the method comprising contacting the CBD with a Lewis-acidic heterogeneous reagent under reaction conditions comprising: (i) an aprotic-solvent system; (ii) a reaction temperature that is greater than a threshold reaction temperature for the Lewis-acidic heterogeneous reagent and the aprotic-solvent system; and (iii) a reaction time that is greater than a threshold reaction time for the Lewis-acidic heterogeneous reagent, the aprotic-solvent system, and the reaction temperature.

In select embodiments, the present disclosure relates to a method for converting CBD into primarily $\Delta^8$-THC, the method comprising contacting the CBD with a Lewis-acidic heterogeneous reagent under reaction conditions comprising: (i) an aprotic-solvent system; (ii) a reaction temperature that is greater than a threshold reaction temperature for the Lewis-acidic heterogeneous reagent and the aprotic-solvent system; and (iii) a reaction time that is greater than a threshold reaction time for the Lewis-acidic heterogeneous reagent, the aprotic-solvent system, and the reaction temperature.

In select embodiments, the present disclosure relates to a method for converting CBD into a composition comprising $\Delta^8$-THC and $\Delta^9$-THC, wherein the composition has a $\Delta^8$-THC:$\Delta^9$-THC ratio that is greater than 1.0:1.0, the method comprising contacting the CBD with a Lewis-acidic heterogeneous reagent under neat reaction conditions comprising: (i) a reaction temperature that is greater than a threshold reaction temperature for the Lewis-acidic heterogeneous reagent; and (ii) a reaction time that is greater than a threshold reaction time for the Lewis-acidic heterogeneous reagent and the reaction temperature.

In select embodiments, the present disclosure relates to a method for converting CBD into primarily $\Delta^8$-THC, the method comprising contacting the CBD with a Lewis-acidic heterogeneous reagent under neat reaction conditions comprising: (i) a reaction temperature that is greater than a threshold reaction temperature for the Lewis-acidic heterogeneous reagent; and (ii) a reaction time that is greater than a threshold reaction time for the Lewis-acidic heterogeneous reagent and the reaction temperature.

In select embodiments, the present disclosure relates to a method for converting CBD into a composition comprising $\Delta^8$-THC and $\Delta^9$-THC, wherein the composition has a $\Delta^8$-THC:$\Delta^9$-THC ratio that is greater than 1.0:1.0, the method comprising contacting the CBD with a Lewis-acidic heterogeneous reagent under reaction conditions comprising: (i) a protic-solvent system; (ii) a reaction temperature that is greater than a threshold reaction temperature for the Lewis-acidic heterogeneous reagent and the protic-solvent system; and (iii) a reaction time that is greater than a threshold reaction time for the Lewis-acidic heterogeneous reagent, the protic-solvent system, and the reaction temperature.

In select embodiments, the present disclosure relates to a method for converting CBD into primarily $\Delta^8$-THC, the method comprising contacting the CBD with a Lewis-acidic heterogeneous reagent under reaction conditions comprising: (i) a protic-solvent system; (ii) a reaction temperature that is greater than a threshold reaction temperature for the Lewis-acidic heterogeneous reagent and the protic-solvent system; and (iii) a reaction time that is greater than a threshold reaction time for the Lewis-acidic heterogeneous reagent, the protic-solvent system, and the reaction temperature.

In select embodiments, the present disclosure relates to a method for converting CBD into $\Delta^8$-THC, the method comprising contacting the CBD with an ion-exchange resin under reaction conditions comprising: (i) a class III solvent; (ii) a reaction temperature that is greater than about 60° C.; and (iii) a reaction time that is greater than about 60 minutes.

In select embodiments, the present disclosure relates to a method for converting CBD into a composition comprising $\Delta^8$-THC and $\Delta^9$-THC, wherein the composition has a $\Delta^8$-THC:$\Delta^9$-THC ratio that is greater than 1.0:1.0, the method comprising contacting the CBD with an aluminosilicate-based reagent under reaction conditions comprising: (i) a class III solvent; (ii) a reaction temperature that is greater than about 70° C.; and (iii) a reaction time that is greater than about 60 minutes.

In the context of the present disclosure, the term "contacting" and its derivatives is intended to refer to bringing the compound of Formula (I) and the Lewis-acidic heterogeneous reagent as disclosed herein into proximity such that a chemical reaction can occur. In some embodiments of the present disclosure, the contacting may be by adding the Lewis-acidic heterogeneous reagent to the compound of Formula (I). In some embodiments, the contacting may be by combining, mixing, or both.

In further select embodiments, the present disclosure relates to a method for converting a compound of Formula (I) into a compound of Formula (II), the method comprising heating a compound of Formula (I)

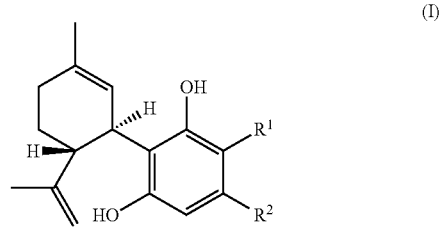

(I)

and a Lewis-acidic heterogeneous reagent in an aprotic-solvent system to provide a compound of Formula (II)

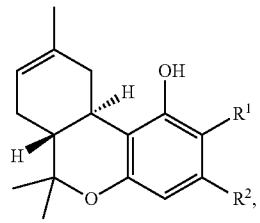

(II)

wherein the Lewis-acidic heterogeneous reagent is acidic alumina, and wherein $R^1$ is hydrogen or COOH, and $R^2$ is hydrogen, $C_1$-$C_{12}$ alkyl, $C_2$-$C_{12}$ alkenyl, $C_2$-$C_{12}$ alkynyl, $(OCH_2CH_2)_{0-6}O(C_1$-$C_8$ alkyl), $(C_0$-$C_4$ alkyl)-$NR^{2a}R^{2b}$, $(C_0$-$C_4$ alkyl)-aryl, $(C_0$-$C_4$ alkyl)-heteroaryl, $(C_0$-$C_4$ alkyl)-cycloalkyl, or $(C_0$-$C_4$ alkyl)-heterocycloalkyl, wherein $R^{2a}R^{2b}$ are each independently hydrogen or $C_1$-$C_6$ alkyl. In an embodiment, $R^1$ is hydrogen. In an embodiment, $R^2$ is $C_3H_7$, $C_5H_{11}$ or $C_7H_{15}$.

In a particular embodiment, the present disclosure relates to a method for converting CBD into $\Delta^8$-THC, the method comprising heating CBD and a Lewis-acidic heterogeneous reagent in an aprotic-solvent system, wherein the Lewis-acidic heterogeneous reagent is acidic alumina.

In a particular embodiment, the present disclosure relates to a method for converting CBDA into $\Delta^8$-THCA, the method comprising heating CBDA and a Lewis-acidic heterogeneous reagent in an aprotic-solvent system, wherein the Lewis-acidic heterogeneous reagent is acidic alumina.

In a particular embodiment, the present disclosure relates to a method for converting CBDV into $\Delta^8$-THCV, the method comprising heating CBDV and a Lewis-acidic heterogeneous reagent in an aprotic-solvent system, wherein the Lewis-acidic heterogeneous reagent is acidic alumina.

In a particular embodiment, the present disclosure relates to a method for converting CBDP into $\Delta^8$-THCP, the method comprising heating CBDP and a Lewis-acidic heterogeneous reagent in an aprotic-solvent system, wherein the Lewis-acidic heterogeneous reagent is acidic alumina.

In the context of the present disclosure, the chemical structures of the compounds of Formula (I), (II) and (III) are shown such that when $R^1$ is COOH, the "A-type" acid form is represented by the chemical formulae shown herein. It is contemplated and encompassed by the disclosure herein that the compounds of Formula (I), (II) and (III) may also be of the "B-type", "AB-type", or any mixture of the "A-type", "B-type" and "AB-type" acidic forms. The compounds of Formula (I), (II) and (III) may also be salts of any such acid forms, such as $Na^+$ or $Ca^{2+}$ salts; ester forms, such as formed by hydroxyl-group esterification to form traditional esters, sulphonate esters, and/or phosphate esters; as well as any cis/trans isomers and/or any stereoisomers.

In the context of the present disclosure, the term "CBD" refers to cannabidiol or, more generally, cannabidiol-type cannabinoids. Accordingly the term "CBD" includes: (i) acid forms, such as "A-type", "B-type", or "AB-type" acid forms; (ii) salts of such acid forms, such as $Na^+$ or $Ca^{2+}$ salts of such acid forms; (iii) ester forms, such as formed by hydroxyl-group esterification to form traditional esters, sulphonate esters, and/or phosphate esters; (iv) various double-bond isomers, such as $\Delta^1$-CBD and $\Delta^6$-CBD as well as cis/trans isomers thereof; and/or (v) various stereoisomers.

In select embodiments of the present disclosure, the CBD is a component of a distillate, an isolate, a concentrate, an extract, or a combination thereof. In select embodiments of the present disclosure, CBD may have the following structural formula:

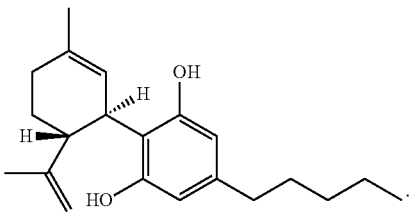 [SMILES: C=C(C)[C@@H]1CCC(C)=C[C@H]1c1c(O)cc(CCCCC)cc1O]

In the context of the present disclosure, the term "$\Delta^9$-THC" refers to $\Delta^9$-tetrahydrocannabinol or, more generally, $\Delta^9$-tetrahydrocannabinol-type cannabinoids. Accordingly the term "$\Delta^9$-THC" includes: (i) acid forms, such as "A-type", "B-type", or "AB-type" acid forms; (ii) salts of such acid forms, such as $Na^+$ or $Ca^{2+}$ salts of such acid forms; (iii) ester forms, such as those formed by hydroxyl-group esterification to form traditional esters, sulphonate esters, and/or phosphate esters; and/or (iv) various stereoisomers. $\Delta^9$-THC may have the following structural formula:

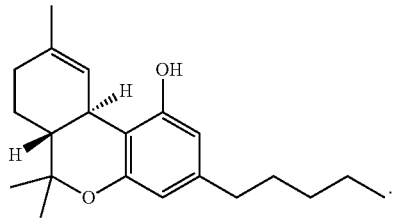 [SMILES: CCCCCc1cc(O)c2c(c1)OC(C)(C)[C@@H]1CCC(C)=C[C@@H]21]

In the context of the present disclosure, the term "$\Delta^8$-THC" refers to $\Delta^8$-tetrahydrocannabinol or, more generally, $\Delta^8$-tetrahydrocannabinol-type cannabinoids. Accordingly the term "$\Delta^8$-THC" includes: (i) acid forms, such as "A-type", "B-type", or "AB-type" acid forms; (ii) salts of such acid forms, such as $Na^+$ or $Ca^{2+}$ salts of such acid forms; and/or (iii) ester forms, such as those formed by hydroxyl-group esterification to form traditional esters, sulphonate esters, and/or phosphate esters; and/or (iv) various stereoisomers. In select embodiments of the present disclosure, $\Delta^8$-THC may have the following structural formula:

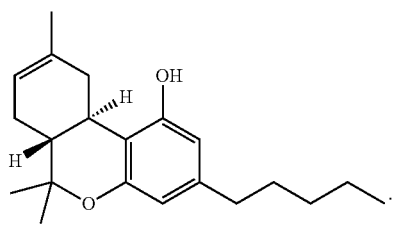 [SMILES: CCCCCc1cc(O)c2c(c1)OC(C)(C)[C@@H]1CC=C(C)C[C@@H]21]

In the context of the present disclosure, the relative quantities of $\Delta^8$ regioisomers and $\Delta^9$ regioisomers (e.g. $\Delta^8$-THC and $\Delta^9$-THC) in a particular composition may be expressed as a ratio—e.g. $\Delta^8:\Delta^9$, or in certain embodiments $\Delta^8$-THC:$\Delta^9$-THC. Those skilled in the art will recognize that a variety of analytical methods may be used to determine such ratios, and the protocols required to implement any such method are within the purview of those skilled in the art. By way of non-limiting example, $\Delta^8:\Delta^9$ ratios may be determined by diode-array-detector high pressure liquid chromatography, UV-detector high pressure liquid chromatography, nuclear magnetic resonance spectroscopy, mass spectroscopy, flame-ionization gas chromatography, gas chromatograph-mass spectroscopy, or combinations thereof.

In select embodiments of the present disclosure, the compositions provided by the methods of the present disclosure have $\Delta^8:\Delta^9$ ratios (e.g. $\Delta^8$-THC:$\Delta^9$-THC ratios) of greater than 1.0:1.0, meaning the quantity of the $\Delta^8$ regioisomer (e.g. $\Delta^8$-THC) in the composition is greater than the quantity of $\Delta^9$ regioisomers (e.g. $\Delta^9$-THC) in the composition. Exemplary $\Delta^8:\Delta^9$ ratios provided by the methods of the present disclosure are described elsewhere herein.

For example, in exemplary reference to $\Delta^8$-THC and $\Delta^9$-THC, the compositions provided by the methods of the present disclosure may have $\Delta^8$-THC:$\Delta^9$-THC ratios on a weight/weight basis (w/w) of: (i) greater than about 2.0:1.0; (ii) greater than about 3.0:1.0; (iii) greater than about 5.0:1.0; (iv) greater than about 10.0:1.0; (v) greater than about 15.0:1.0; (vi) greater than about 20.0:1.0; (vii) greater than about 50.0:1.0; or (viii) greater than about 100.0:1.0. In an embodiment, the $\Delta^8$-THC:$\Delta^9$-THC ratio (w/w) is between about 100:1 and about 1.5:1, more particularly between about 50:1 and about 2:1, and more particularly still between about 25:1 and about 5:1. In an embodiment, the $\Delta^8$-THC:$\Delta^9$-THC ratio (w/w) is about 50:1, about 45:1, about 40:1, about 35:1, about 30:1, about 25:1, about 24:1, about 23:1, about 22:1, about 21:1, about 20:1, about 19:1, about 18:1, about 17:1, about 16:1, about 15:1, about 14:1, about 13:1, about 12:1, about 11:1, about 10:1, about 9:1, about 8:1, about 7:1, about 6:1, about 5:1, about 4:1, about 3:1, or about 2:1.

In a particular embodiment of the methods disclosed herein, the Lewis-acidic heterogeneous reagent is acidic alumina and the $\Delta^8:\Delta^9$ ratio (w/w) is any of those referenced in the preceding paragraph. In a further particular embodiment of the methods disclosed herein, the Lewis-acidic heterogeneous reagent is acidic alumina, the aprotic-solvent system is heptane, and the $\Delta^8:\Delta^9$ ratio (w/w) is any of those referenced in the preceding paragraph. In an embodiment, the Lewis-acidic heterogeneous reagent is acidic alumina, the aprotic-solvent system is heptane, and the $\Delta^8:\Delta^9$ ratio (w/w) is between about 25:1 and about 5:1. In an embodiment, the Lewis-acidic heterogeneous reagent is acidic alumina, the aprotic-solvent system is heptane, and the $\Delta^8:\Delta^9$ ratio (w/w) is about 25:1, about 24:1, about 23:1, about 22:1, about 21:1, about 20:1, about 19:1, about 18:1, about 17:1, about 16:1, about 15:1, about 14:1, about 13:1, about 12:1, about 11:1, about 10:1, about 9:1, about 8:1, about 7:1, about 6:1, about 5:1. In an embodiment of such methods, the compound of Formula (I) is CBD and the compound of Formula (II) is $\Delta^8$-THC, such that the $\Delta^8:\Delta^9$ ratios referenced in this paragraph are $\Delta^8$-THC:$\Delta^9$-THC ratios.

In the context of the present disclosure, converting the compound of Formula (I) into "primarily" a compound of Formula (II) refers to converting the compound for Formula (I) into exclusively the compound of Formula (II) or into a composition in which the $\Delta^8$ regioisomer is present to a greater extent than any other reaction product, including for example the $\Delta^9$ regioisomer. In select embodiments of the present disclosure, converting the compound of Formula (I) into the compound of Formula (II) may yield a product mixture which is at least: (i) 50% compound of Formula (II) on a molar basis; (ii) 60% compound of Formula (II) on a molar basis; (iii) 70% compound of Formula (II) on a molar basis; (iv) 80% compound of Formula (II) on a molar basis; (v) 90% compound of Formula (II) on a molar basis; or (vi) 95% compound of Formula (II) on a molar basis. In select embodiments of the present disclosure, converting the compound of Formula (I) into the compound of Formula (II) may yield a product mixture which is at least 50%, at least 55%, at least 60%, at least 65%, at least 70%, at least 75%, at least 80%, at least 85%, at least 90%, at least 95%, at least 96%, at least 97%, or more compound of Formula (II) on a weight basis. Importantly converting the compound of Formula (I) into a composition in which the compound of Formula (II) is the primary product does not necessarily imply that the compound of Formula (I) is the most prevalent component of a reaction composition, as other constituents derived from the starting material may be more prevalent. For example, the compound of Formula (II) may be the primary product in a reaction mixture that includes primarily unreacted compound of Formula (I).

In the context of the present disclosure, a Lewis-acid heterogeneous reagent is one which: (i) comprises one or more sites that are capable of accepting an electron pair from an electron pair donor; and (ii) is substantially not mono-phasic with the reagent (i.e. compound of Formula (I)). Likewise, in the context of the present disclosure, a Brønsted-acid heterogeneous reagent is one which: (i) comprises one or more sites that are capable of donating a proton to a proton-acceptor; and (ii) is substantially not mono-phasic with the starting material and/or provides an interface where one or more chemical reaction takes place. Importantly, the term "reagent" is used in the present disclosure to encompass both reactant-type reactivity (i.e. wherein the reagent is at least partly consumed as reactant is converted to product) and catalyst-type reactivity (i.e. wherein the reagent is not substantially consumed as reactant is converted to product).

In the context of the present disclosure, the acidity of a Lewis-acid heterogeneous reagent and/or a Brønsted-acid heterogeneous reagent may be characterized by a variety of parameters, non-limiting examples of which are summarized in the following paragraphs.

As will be appreciated by those skilled in the art who have benefitted from the teachings of the present disclosure, determining the acidity of heterogeneous solid acids may be significantly more challenging than measuring the acidity of homogenous acids due to the complex molecular structure of heterogeneous solid acids. The Hammett acidity function ($H_0$) has been applied over the last 60 years to characterize the acidity of solid acids in non-aqueous solutions. This method utilizes organic indicator bases, known as Hammett indicators, which coordinate to the accessible acidic sites of the solid acid upon protonation. Typically, a color change is observed during titration with an additional organic base (e.g. n-butylamine), which is measured by UV-visible spectroscopy to quantify acidity. Multiple Hammett indicators with pKa values ranging from +6.8 (e.g. neutral red) to −8.2 (e.g. anthraquinone) are tested with a given solid acid to determine the quantity and strength of acidic sites, which is typically expressed in mmol per gram of solid acid for each indicator. Hammett acidity values may not provide a complete characterization of acidity. For example, accurate measurement of acidity may rely on the ability of the Hammett indicator to access the interior acidic sites within the solid acid. Some solid acids may have pore sizes that permit the passage of small molecules but prevent larger molecules from accessing the interior of the acid. H-ZSM-5 may be a representative example, wherein larger Hammett indicators such as anthraquinone may not be able to access interior acidic sites, which may lead to an incomplete measure of its total acidity.

Temperature-Programmed Desorption (TPD) is an alternate technique for characterizing the acidity of heterogeneous solid acids. This technique typically utilizes an organic base with small molecular size (e.g. ammonia, pyridine, n-propylamine), which may react with the acid sites on the exterior and interior of the solid acid in a closed system. After the solid acid is substantially saturated with organic base, the temperature is increased and the change in organic base concentration is monitored gravimetrically, volumetrically, by gas chromatography, or by mass spectrometry. The amount of organic base desorbing from the solid acid above some characteristic temperature may be interpreted as the acid-site concentration. TPD is often considered more representative of total acidity for solid acids compared to the Hammett acidity function, because the selected organic base is small enough to bind to acidic sites on the interior of the solid acid.

In select embodiments of the present disclosure, TPD values are reported with respect to ammonia. Those skilled in the art who have benefited from the teachings of the present disclosure will appreciate that ammonia may have the potential disadvantage of overestimating acidity, because its small molecular size enables access to acidic sites on the interior of the solid acid that are not accessible to typical organic substrates being employed for chemical reactions (i.e. ammonia may fit into pores that CBD cannot). Despite this disadvantage, TPD with ammonia is still considered a useful technique to compare total acidity of heterogeneous solid acids (larger $NH_3$ absorption values correlate with stronger acidity).

Another commonly used method for characterizing the acidity of heterogeneous solid acids is microcalorimetry. In this technique, the heat of adsorption is measured when acidic sites on the solid acid are neutralized by addition of a base. The measured heat of adsorption is used to characterize the strength of Brønsted-acid sites (the larger the heat of adsorption, the stronger the acidic site, such that more negative values correlate with stronger acidity).

Microcalorimetry may provide the advantage of being a more direct method for the determination of acid strength when compared to TPD. However, the nature of the acidic sites cannot be determined by calorimetry alone, because adsorption may occur at Brønsted sites, Lewis sites, or a combination thereof. Further, experimentally determined heats of adsorption may be inconsistent in the literature for a given heterogeneous acid. For example, $\Delta H_{O_{ads}}$ $NH_3$ values between about 100 kJ/mol and about 200 kJ/mol have been reported for H-ZSM-5. Thus, heats of adsorption determined by microcalorimetry may be best interpreted in combination with other acidity characterization methods such as TPD to properly characterize the acidity of solid heterogeneous acids.

Non-limiting examples of: (i) Hammett acidity values; (ii) TPD values with reference to ammonia; and (iii) microcalorimetry values with reference to ammonia, for a selection of Lewis-acidic heterogeneous reagents in accordance with the present disclosure are set out in Table 1.

TABLE 1

Non-limiting examples of: (i) Hammett acidity values; (ii) TPD values with reference to ammonia; and (iii) microcalorimetry values with reference to ammonia.

| Acid Reagent | Classification | Hammett Value ($H_0$) | TPD $NH_3$ (mmol/g) | $\Delta H^\circ_{ads}$ $NH_3$ (kJ/mol) |
|---|---|---|---|---|
| Amberlyst-35 | Ion-exchange resin | −5.6 | 5.2] | −117 |
| Amberlyst-15 | Ion-exchange resin | −4.6 | 4.6 | −116 |
| H-ZSM-5 | Microporous aluminosilicate (zeolite) | −5.6 < $H_0$ < −3.0 | 1.0] | −145 |
| H-Beta | Microporous aluminosilicate (zeolite) | — | 0.65 | −120 |
| Al-MCM-41 | Mesoporous aluminosilicate | —. | 0.26 | —. |
| Montmorillonite (K30) | Phyllosilicate (clay) | −1.5 < $H_0$ < +3.2 | 0.18 | — |

In select embodiments of the present disclosure, the Lewis-acidic heterogeneous reagent may have a Hammett-acidity value ($H_o$) of between about −8.0 and about 0.0. For example, the Lewis-acidic heterogeneous reagent may have a Hammett-acidity value ($H_o$) of between: (i) about −8.0 and about −7.0; (ii) about −7.0 and about −6.0; (iii) about −6.0 and about −5.0; (iv) about −5.0 and about −4.0; (v) about −4.0 and about −3.0; (vi) about −3.0 and about −2.0; (vii) about −2.0 and about −1.0; or (viii) about −1.0 and about 0.

In select embodiments of the present disclosure, the Lewis-acidic heterogeneous reagent may have a temperature-programmed desorption value of between about 7.5 and about 0.0 as determined with reference to ammonia ($TPD_{NH3}$). For example, the Lewis-acidic heterogeneous reagent may have a temperature-programmed desorption value of between: (i) about 7.5 and about 6.5 as determined with reference to ammonia ($TPD_{NH3}$); (ii) about 6.5 and about 5.5 as determined with reference to ammonia ($TPD_{NH3}$); (iii) about 5.5 and about 4.5 as determined with reference to ammonia ($TPD_{NH3}$); (iv) about 4.5 and about 3.5 as determined with reference to ammonia ($TPD_{NH3}$); (v) about 3.5 and about 2.5 as determined with reference to ammonia ($TPD_{NH3}$); (vi) about 2.5 and about 1.5 as determined with reference to ammonia ($TPD_{NH3}$); (vii) about 1.5 and about 0.5 as determined with reference to ammonia ($TPD_{NH3}$); or (viii) about 0.5 and about 0.0 as determined with reference to ammonia ($TPD_{NH3}$).

In select embodiments of the present disclosure, the Lewis-acidic heterogeneous reagent may have a heat of absorption value of between about −165 and about −100 as determined with reference to ammonia ($\Delta H^\circ_{ads\ NH3}$). For example, the Lewis-acidic heterogeneous reagent may have a heat of absorption value of between: (i) about −165 and about −150 as determined with reference to ammonia ($\Delta H^\circ_{ads\ NH3}$); (ii) about −150 and about −135 as determined with reference to ammonia ($\Delta H^\circ_{ads\ NH3}$); (iii) about −135 and about −120 as determined with reference to ammonia ($\Delta H^\circ_{ads\ NH3}$); (iv) about −120 and about −105 as determined with reference to ammonia ($\Delta H^\circ_{ads\ NH3}$); or (v) about −105 and about −100 as determined with reference to ammonia ($\Delta H^\circ_{ads\ NH3}$).

In select embodiments of the present disclosure, the Lewis-acidic heterogeneous reagent may comprise an ion-exchange resin, a microporous silicate such as a zeolite (natural or synthetic), a mesoporous silicate (natural or synthetic) and/or a phyllosilicate (such as montmorillonite).

Lewis-acidic heterogeneous reagents that comprise an ion-exchange resin may comprise, for example, Amberlyst polymeric resins (also commonly referred to as "Amberlite" resins). Amberlyst polymeric resins include but are not limited to Amberlyst-15, 16, 31, 33, 35, 36, 39, 46, 70, CH10, CH28, CH43, M-31, wet forms, dry forms, macroreticular forms, gel forms, H⁺ forms, Na⁺ forms, or combinations thereof). In select embodiments of the present disclosure, the Lewis-acidic heterogeneous reagent may comprise an Amberlyst resin that has a surface area of between about 20 m²/g and about 80 m²/g. In select embodiments of the present disclosure, the Lewis-acidic heterogeneous reagent may comprise an Amberlyst resin that has an average pore diameter of between about 100 Å and about 500 Å. In select embodiments of the present disclosure, the Lewis-acidic heterogeneous reagent may comprise Amberlyst-15. Amberlyst-15 is a styrene-divinylbenzene-based polymer with sulfonic acid functional groups linked to the polymer backbone. Amberlyst-15 may have the following structural formula:

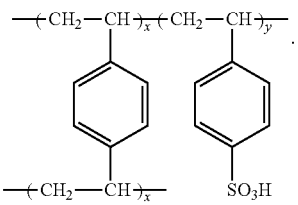

In an embodiment of the methods disclosed herein, the Lewis-acidic heterogeneous reagent is an Amberlyst polymeric resin which is Amberlyst-15, 16, 31, 33, 35, 36, 39, 46, 70, CH10, CH28, CH43 or M-31, or a H+ or Na+ form thereof, or any combination thereof. In select embodiments of the disclosed methods, the Amberlyst polymeric resin is other than Amberlyst-15.

Lewis-acidic heterogeneous reagents that comprise an ion-exchange resin may comprise, for example, Nafion polymeric resins. Nafion polymeric resins may include but are not limited to Nafion-NR50, N115, N117, N324, N424, N1110, SAC-13, powder forms, resin forms, membrane forms, aqueous forms, dispersion forms, composite forms, H⁺ forms, Na⁺ forms, or combinations thereof.

In an embodiment of the methods disclosed herein, the Lewis-acidic heterogeneous reagent is a Nafion polymeric resin which is Nafion-NR50, N115, N117, N324, N424 or N1110, SAC-13, or a H+ or Na+ form thereof, or any combination thereof. In select embodiments of the disclosed methods, the Nafion polymeric resin is other than Nafion-SAC-13.

Lewis-acidic heterogeneous reagents that comprise microporous silicates (e.g. zeolites) may comprise, for example, natural and synthetic zeolites. Lewis-acidic heterogeneous reagents that comprise mesoporous silicates may comprise, for example, Al-MCM-41 and/or MCM-41. Lewis-acidic heterogeneous reagents that comprise phyllosilicates may comprise, for example, montmorillonite. A commonality amongst these materials is that they are all silicates. Silicates may include but are not limited to Al-MCM-41, MCM-41, MCM-48, SBA-15, SBA-16, ZSM-5, ZSM-11, ZSM-22, ZSM-23, ZSM-35, SAPO-11, SAPO-34, SSZ-13, TS-1, KIT-5, KIT-6, FDU-12, Beta, X-type, Y-type, Linde type A, Linde type L, Linde type X, Linde type Y, Faujasite, USY, Mordenite, Ferrierite, Montmorillonite K10, K30, KSF, Clayzic, bentonite, H⁺ forms, Na⁺ forms, or combinations thereof. Zeolites are commonly used as adsorbents and catalysts (e.g. in fluid catalytic cracking and hydrocracking in the petrochemical industry). Although zeolites are abundant in nature, the zeolites used for commercial and industrial processes are often made synthetically. Their structural framework consists of $SiO_4$ and $AlO_4^-$ tetrahedra, which are combined in specific ratios with an amine or tetraalkylammonium salt "template" to give a zeolite with unique acidity, shape and pore size. The Lewis and/or Brønsted-Lowry acidity of zeolites can typically be modified using two approaches. One approach involves adjusting the Si/Al ratio. Since an $AlO_4^-$ moiety is unstable when attached to another $AlO_4^-$ unit, it is necessary for them to be separated by at least one $SiO_4$ unit. The strength of the individual acidic sites may increase as the $AlO_4^-$ units are further separated Another approach involves cation exchange. Since zeolites contain charged $AlO_4^-$ species, an extra-framework cation such as $Na^+$ is required to maintain electroneutrality. The extra-framework cations can be replaced with protons to generate the "H-form" zeolite, which has stronger Brønsted acidity than its metal cation counterpart.

In select embodiments of the present disclosure, the Lewis-acidic heterogeneous reagent may comprise "$H^+$-form" zeolites "$Na^+$-form" zeolites, and/or a suitable mesoporous material. By way of non-limiting example, the acidic heterogeneous reagent may comprise Al-MCM-41, MCM-41, MCM-48, SBA-15, SBA-16, ZSM-5, ZSM-11, ZSM-22, ZSM-23, ZSM-35, SAPO-11, SAPO-34, SSZ-13, TS-1, KIT-5, KIT-6, FDU-12, Beta, X-type, Y-type, Linde type A, Linde type L, Linde type X, Linde type Y, Faujasite, USY, Mordenite, Ferrierite, montmorillonite, bentonite, or combinations thereof. Suitable mesoporous materials and zeolites may have a pore diameter ranging from about 0.1 nm to about 100 nm, particle sizes ranging from about 0.1 μm to about 50 μm, Si/Al ratio ranging from 5-1500, and any of the following cations: $H^+$, $Na^+$, $K^+$, $NH_4^+$, $Rb^+$, $Cs^+$, $Ag^+$. Furthermore, suitable zeolites may have frameworks that are substituted with or coordinated to other atoms including, for example, titanium, copper, iron, cobalt, manganese, chromium, zinc, tin, zirconium, and gallium.

In an embodiment of the methods disclosed herein, the Lewis-acidic heterogeneous reagent is a microporous silicate and is a zeolite which is ZSM 5, ZSM 11, ZSM-22, ZSM-23, ZSM-35, SAPO-11, SAPO-34, SSZ-13, TS-1, Beta, X-type, Y-type, Linde type A, Linde type L, Linde type X, or Linde type Y, or a H+ or Na+ form thereof, or any combination thereof. In select embodiments of the disclosed methods, the microporous silicate and is other than Zeolite Y, Zeolite Beta, or SAPO-11.

In an embodiment of the methods disclosed herein, the Lewis-acidic heterogeneous reagent is a mesoporous silicate and is Al-MCM-41, MCM-41, MCM-48, SBA-15, SBA-16, KIT-5, KIT-6, FDU-12, or any combination thereof.

In an embodiment of the methods disclosed herein, the Lewis-acidic heterogeneous reagent is a phyllosilicate and is Faujasite, Mordenite, Ferrierite, Montmorillonite K10, Montmorillonite K20, Montmorillonite K30, Montmorillonite KSF, Clayzic, bentonite, or any combination thereof. In a particular embodiment, the Lewis-acidic heterogeneous reagent to be used in the methods herein is Montmorillonite K10, Montmorillonite K20, Montmorillonite K30 or Montmorillonite KSF.

In select embodiments of the present disclosure, the Lewis-acidic heterogeneous reagent is H-ZSM-5 (P-38 (Si/Al=38), $H^+$ form, ~5 angstrom pore size, 2 μm particle size), Na-ZSM-5 (P-38 (Si/Al=38), $Na^+$ form, ~5 angstrom pore size, 2 μm particle size), Al-MCM-41 (aluminum-doped Mobil Composition of Matter No. 41; e.g., P-25 (Si/Al=25), 2.7 nm pore diameter), or combinations thereof.

In select embodiments of the present disclosure, the Lewis-acidic heterogeneous reagent is Al-MCM-41 and the compound of Formula (I) is comprised in a cannabis distillate. In these embodiments, the reaction conditions may be chosen to selectively form compounds of Formula (II). More particularly, in select embodiments of the present disclosure, the Lewis-acidic heterogeneous reagent is Al-MCM-41 and the compound of Formula (I) is CBD comprised in a CBD distillate. In these embodiments, the reaction conditions may be chosen to selectively form $\Delta^8$-THC.

In select embodiments of the present disclosure, the Lewis-acidic heterogeneous reagent is acidic alumina. Acidic alumina is also known as activated alumina and is a highly porous aluminum oxide often used in chromatography separation of, for example, phenols, sulphonic acids, carboxylic acids and amino acids. In an embodiment, the acidic alumina has a pH of less than about 6.5, about 6, about 5.5, about 5.0, about 4.5 or about 4.0. In an embodiment, the acidic alumina has a pH of less than about 5.5, about 5.0, about 4.5 or about 4.0. In an embodiment, the acidic alumina, has a pH of about 2.5, about 3.0, about 3.5, about 4.0, about 4.5, about 5.0, about 5.5, about 6.0, or about 6.5.

In embodiments where the Lewis-acidic heterogeneous reagent is acidic alumina, the methods herein may further comprise drying the acidic alumina prior to use in the methods disclosed herein. In an embodiment, the acidic alumina is dried until immediately before use in the methods disclosed herein, such as until within 4 hours, within 2 hours, within 1 hour, or less prior to use in the methods disclosed herein. Drying may be by any suitable means. In an embodiment, the drying is by heating the acidic alumina, such as to temperatures of above 150° C. In an embodiment, drying may be at about 150° C., about 160° C., about 170° C., about 180° C., about 190° C., about 200° C., about 210° C., about 220° C., about 230° C., about 240° C., or about 250° C. In an embodiment, the drying is performed for about 1 hour, about 2 hours, about 3 hours, about 4 hours, about 5 hours, about 6 hours, about 7 hours, about 8 hours, about 9 hours, about 10 hours, about 11 hours, about 12 hours, or longer. In an embodiment, the dried acidic alumina contains less than 1.5% w/w water, more particularly less than 1.0% w/w water, even more particularly less than 0.5% w/w water, and more particularly still less than 0.25% w/w water or an undetectable level of water.

In select embodiments of the present disclosure, the Lewis-acidic heterogeneous reagent is acidic alumina and the compound of Formula (I) is comprised in a cannabis isolate. In these embodiments, the reaction conditions may be chosen to selectively form the compound of Formula (II). In an embodiment, the method comprises heating the compound of Formula (I) and acidic alumina in an aprotic-solvent system. More particularly, in select embodiments of the present disclosure, the Lewis-acidic heterogeneous reagent is acidic alumina and the compound of Formula (I) is CBD comprised in a CBD isolate. In these embodiments, the reaction conditions may be chosen to selectively form $\Delta^8$-THC. In an embodiment, the method comprises heating CBD and acidic alumina in an aprotic-solvent system.

In select embodiments of the present disclosure, the compound of Formula (I) is contacted with a Lewis-acidic reagent in a protic-solvent system. By way of non-limiting example a protic-solvent system may comprise methanol, ethanol, 1-propanol, 2-propanol, 1-butanol, 2-butanol, water, acetic acid, formic acid, 3-methyl-1-butanol, 2-methyl-1-propanol, 1-pentanol, nitromethane, or a combination thereof.

In select embodiments of the present disclosure, the compound of Formula (I) is contacted with a Lewis-acidic reagent in an aprotic-solvent system. By way of non-limiting example an aprotic-solvent system may comprise acetone, dimethyl sulfoxide, ethyl acetate, dichloromethane, chloroform, toluene, pentane, heptane, hexane, diethyl ether, tert-butyl methyl ether, tetrahydrofuran, dioxane, dimethylformamide, dimethylacetamide, N-methylpyrrolidone, anisole, butyl acetate, cumene, ethyl formate, isobutyl acetate, isopropyl acetate, methyl acetate, methylethylketone, methylisobutylketone, propyl acetate, cyclohexane, para-xylene, meta-xylene, ortho-xylene, 1,2-dichloroethane, or a combination thereof. As will be appreciated by those skilled in the art who have benefitted from the present disclosure, aprotic solvent systems may comprise small amounts of protic species, the quantities of which may be influenced by the extent to which drying and/or degassing procedures are employed.

In select embodiments, the methods of the present disclosure may be conducted in the presence of a class III solvent. Heptane, ethanol, acetone and combinations thereof are non-limiting examples of class III solvents. In select embodiments of the methods disclosed herein, the aprotic-solvent system is heptane. In select embodiments of the methods disclosed herein, the aprotic-solvent system is acetone.

In select embodiments, any of the solvent systems described herein may include a co-solvent. By "co-solvent", it is meant a solvent that is included in addition to the primary solvent in the solvent system. By "primary solvent" it is meant the majority solvent by weight and/or volume or the solvent primarily involved in controlling the reaction. In an embodiment, the co-solvent is a solvent with a higher polarity than the primary solvent. In an embodiment, the co-solvent is a solvent with a lower polarity than the primary solvent. In an embodiment, the solvent systems herein employ a co-solvent having increased polarity over the primary solvent when the substituent of $R^2$ is hydrogen or a short hydrocarbon chain (e.g. $C_1H_3$, $C_2H_5$, $C_3H_7$ or $C_4H_9$). In an embodiment, the solvent systems herein employ a co-solvent having increased polarity over the primary solvent when the substituent of $R^1$ is COOH.

In select embodiments, the methods of the present disclosure may be conducted in the presence of an aprotic-solvent system as described herein, and a co-solvent may be included in the aprotic-solvent system. In an embodiment, the co-solvent is one having an increased polarity as compared to the primary solvent in the aprotic-solvent system. For example and without limitation, in an embodiment the aprotic-solvent system comprises heptane as the primary solvent and includes a co-solvent that is ethyl acetate, TBME, acetone, or any combination thereof. In an embodiment the aprotic-solvent system comprises heptane and ethyl acetate. In an embodiment the aprotic-solvent system comprises heptane and TBME. In an embodiment the aprotic-solvent system comprises heptane and acetone.

In select embodiments of the present disclosure, the compound of Formula (I) is contacted with a Lewis-acidic reagent under neat reaction conditions. As will be appreciated by those skilled in the art who have benefitted from the present disclosure, neat reaction conditions are substantially free of solvent.

In select embodiments of the present disclosure, the compound of Formula (I) is contacted with a Lewis-acidic reagent under reaction conditions characterized by: (i) a reaction temperature that is greater than a threshold reaction temperature for the particular Lewis-acidic heterogeneous reagent and the particular solvent system; and (ii) a reaction time that is greater than a threshold reaction time for the particular Lewis-acidic heterogeneous reagent, the particular solvent system, and the particular reaction temperature.

As evidenced by the examples of the present disclosure, the acidity of the Lewis-acidic heterogeneous reagent and the characteristics of the solvent system impact the threshold reaction-temperature and the threshold reaction time. Without being bound to any particular theory, the examples of the present disclosure appear to indicate that aprotic solvent-systems, increased acidity, increased reaction temperatures, and/or increased reaction times appear to favor $\Delta^8$ regioisomer formation over $\Delta^9$ regioisomer formation. Importantly, these reaction parameters appear to be dependent variables in that altering one may impact the others. As such, each reaction temperature may be considered in reference to a threshold reaction temperature for the particular Lewis-acidic heterogeneous reagent, the particular solvent system, and the particular reaction time associated with the reaction. Likewise, each reaction time in the present disclosure may be considered in reference to a threshold reaction time for the particular Lewis-acidic heterogeneous reagent, the particular solvent system, and the particular reaction temperature.

With respect to reaction temperatures, by way of non-limiting example, the methods of the present disclosure may involve reaction temperatures ranging from about 0° C. to about 200° C. For example, methods of the present disclosure may involve reaction temperatures between: (i) about 5° C. and about 15° C.; (ii) about 15° C. and about 25° C.; (iii) about 25° C. and about 35° C.; (iv) about 35° C. and about 45° C.; (v) about 45° C. and about 55° C.; (vi) about 55° C. and about 65° C.; (vii) about 65° C. and about 75° C.; (viii) about 75° C. and about 85° C.; (ix) about 85° C. and about 95° C.; (x) about 95° C. and about 105° C.; (xi) about 105° C. and about 115° C.; or a combination thereof. In particular embodiments, the disclosed methods involve performing the reaction under heated conditions. The heating step may occur, for example, at a temperature in a range from about 65° C. to about 125° C. In an embodiment, the heating step may occur at a temperature from about 80° C. to about 110° C., more particularly from about 80° C. to about 100° C., even more particularly from about 80° C. to about 95° C., and more particularly still from about 85° C. to about 95° C. Of course, the reaction temperature may be varied over the course of the reaction while still being characterized as one or more of the foregoing reaction temperatures. Heating at any of the temperatures disclosed herein can be in reference to either the actual reaction temperature or the heating element set point (e.g. jacket temperature).

In select embodiments of the present disclosure, the method comprises heating a compound of Formula (I) and acidic alumina in an aprotic-solvent system. In an embodiment, the aprotic-solvent system is heptane. In embodiments of such methods, the heating step may occur at any temperature described herein that is above room temperature. In an embodiment, the heating step may occur at a temperature in a range from about 65° C. to about 125° C. In an embodiment, the heating step may occur at a temperature in a range from about 80° C. to about 110° C., more particularly from about 80° C. to about 100° C., even more particularly from about 80° C. to about 95° C., and more particularly still from about 85° C. to about 95° C. In an embodiment, the heating step may occur at about 70° C., about 71° C., about 72° C., about 73° C., about 74° C., about 75° C., about 76° C., about 77° C., about 78° C., about 79° C., about 80° C., about 81° C., about 82° C., about 83° C., about 84° C., about 85° C., about 86° C., about 87° C., about 88° C., about 89° C., about 90° C., about 91° C., about 92° C., about 93° C., about 94° C., about 95° C., about 96° C., about 97° C., about 98° C., about 99° C., about 100° C., about 101° C., about 102° C., about 103° C., about 104° C., about 105° C., about 106° C., about 107° C., about 108° C., about 109° C., or about 110° C. Heating at any of these temperatures can be in reference to either the actual reaction temperature or the heating element set point (e.g. jacket temperature).

In embodiments of the methods disclosed herein involving compounds of Formula (I) in which $R^1$ is COOH, the heating step may be performed at lower temperatures to avoid decarboxylation. For example, in such embodiments the heating step may occur at a maximum temperature of about 110° C., or even 100° C. In an embodiment, the heating step may occur in a range from about 65° C. to about 110° C., more particularly from about 75° C. to about 100° C., and more particularly still from about 75° C. to about 90° C.

With respect to reaction times, by way of non-limiting example, methods of the present disclosure may involve reaction times ranging from about 30 minutes to about 85 hours. For example, methods of the present disclosure may involve reaction times between: (i) 30 minutes and about 1 hour; (ii) about 1 hour and about 5 hours; (iii) about 5 hours and about 10 hours; (iv) about 10 hours and 25 hours; (v) about 25 hours and about 40 hours; (vi) about 40 hours and about 55 hours; (vii) about 55 hours and about 70 hours; or (viii) about 70 hours and about 85 hours. In some embodiments, the reaction time may be between about 1 hour and about 48 hours, more particularly between about 2 hours and about 36 hours, and more particularly still between about 6 hours and about 30 hours.

In select embodiments of the present disclosure, the method comprises heating a compound of Formula (I) and acidic alumina in an aprotic-solvent system. In an embodiment, the aprotic-solvent system is heptane. In embodiments of such methods, the reaction time may be between about 1 hour and about 48 hours, more particularly between about 2 hours and about 36 hours, and more particularly still between about 6 hours and about 30 hours. In an embodiment, the reaction time may is about 30 minutes, about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 25 hours, about 26 hours, about 27 hours, about 28 hours, about 29 hours, about 30 hours, about 31 hours, about 32 hours, about 33 hours, about 34 hours, about 35 hours, or about 36 hours.

In select embodiments, the methods disclosed herein are performed under inert atmosphere. The inert atmosphere may, for example, be provided by an inert gas. In exemplary embodiments, the inert gas may be nitrogen, helium, neon, argon, krypton, xenon or radon. In an embodiment of the methods herein, the inert atmosphere is provided by nitrogen ($N_2$) or argon. In a particular embodiment, the inert atmosphere is provided by nitrogen ($N_2$). In a particular embodiment, an inert atmosphere is used when $R^1$ is COOH in the compound of Formula (I).

In select embodiments of the present disclosure, the method comprises heating a compound of Formula (I) and acidic alumina in an aprotic-solvent system. In an embodiment, the aprotic-solvent system is heptane. In embodiments of such methods, the heating step occurs in an inert atmosphere, such as in an inert gas as described herein. In an embodiment, the inert gas is nitrogen or argon. In a particular embodiment, the inert gas is nitrogen.

In select embodiments of the present disclosure, the methods are performed under agitation. In an embodiment, the methods are performed in a rotating bed reactor or in a stirred tank reactor. Without limitation, the rotation speed of the rotary bed reactor to be used in the methods of the present disclosure may be a speed between about 100 rpm and about 1000 rpm, and more particularly between about 250 rpm and about 750 rpm. In an embodiment, the rotation speed of the rotary bed reactor to be used in the methods of the present disclosure is about 100 rpm, about 150 rpm, about 200 rpm, about 250 rpm, about 300 rpm, about 350 rpm, about 400 rpm, about 450 rpm, about 500 rpm, about 550 rpm, about 600 rpm, about 650 rpm, about 700 rpm, about 750 rpm, about 800 rpm, about 850 rpm, about 900 rpm, about 950 rpm, and about 1000 rpm.

In select embodiments of the present disclosure, the method comprises heating a compound of Formula (I) and acidic alumina in an aprotic-solvent system. In an embodiment, the aprotic-solvent system is heptane. In embodiments of such methods, the heating step may be performed under agitation, such as in a rotating bed reactor or in a stirred tank reactor. In an embodiment, a rotating bed reactor may be used and the acidic alumina (solid) is within the reactor bed. In an embodiment, the rotation speed of the rotary bed reactor is between about 100 rpm and about 1000 rpm, and more particularly between about 250 rpm and about 750 rpm.

In select embodiments, methods of the present disclosure may involve compound of Formula (I) concentrations ranging from about 0.001 M to about 2 M. For example methods of the present disclosure may involve reactant concentrations of: (i) between about 0.01 M and about 0.1 M; (ii) between about 0.1 M and about 0.5 M; (iii) between about 0.5 M and about 1.0 M; (iv) between about 1.0 M and about 1.5 M; or (v) between about 1.5 M and about 2.0 M.

In select embodiments, methods of the present disclosure may involve Lewis-acidic heterogeneous reagent loadings ranges from about 0.1 molar equivalents to about 100 molar equivalents relative to the compound of Formula (I). For example methods of the present disclosure may involve Lewis-acidic heterogeneous reagent loadings of: (i) between about 0.1 molar equivalents to about 1.0 molar equivalents, relative to the compound of Formula (I); (ii) 1.0 molar equivalents to about 5.0 molar equivalents, relative to the compound of Formula (I); (iii) 5.0 molar equivalents to about 10.0 molar equivalents, relative to the compound of Formula (I); (iv) 10.0 molar equivalents to about 50.0 molar equivalents, relative to the compound of Formula (I); or (v) 50.0 molar equivalents to about 100.0 molar equivalents, relative to the compound of Formula (I). In certain embodiments, the Lewis-acidic heterogeneous reagent is in an amount of between about 0.1 to about 100 molar equivalents with respect to the compound of Formula (I), more particularly between about 1.0 to about 50 molar equivalents, and more particularly still between about 1.0 to about 25 molar equivalents. In a particular, the Lewis-acidic heterogeneous reagent is in an amount of between about 1.0 to about 10 molar equivalents with respect to the compound of Formula (I), and more particularly still between about 1.0 to about 5.0 molar equivalents. In select embodiments, the Lewis-acidic heterogeneous reagent is in an amount of about 0.1, about 0.25, about 0.5, about 0.75, about 1.0, about 2.5, about 5.0, about 10, about 15, about 20, about 25, about 50, about 75 or about 100 molar equivalents with respect to the compound of Formula (I). In an embodiment, the compound of Formula (I) is CBD.

In select embodiments of the present disclosure, the methods involve using a molar excess of the Lewis-acidic heterogeneous reagent relative to the compound of Formula (I). In an embodiment, the molar excess is about 2, about 3, about 4, about 5, about 6, about 7, about 8, about 9, about 10, about 15, about 25, about 50 or more molar equivalents of Lewis-acidic heterogeneous reagent with respect to the compound of Formula (I). In an embodiment, the compound of Formula (I) is CBD. In an embodiment, the compound of Formula (I) is CBD and the Lewis-acidic heterogeneous reagent is acidic alumina.

In select embodiments of the present disclosure, the method comprises heating a compound of Formula (I) and acidic alumina in an aprotic-solvent system. In an embodiment, the aprotic-solvent system is heptane. In embodiments of such methods, the heating step may be performed using a molar excess of the acidic alumina relative to the compound of Formula (I). In an embodiment, the molar excess is about 2, about 3, about 4, about 5, about 6, about 7, about 8, about 9, about 10, about 15, about 25, about 50 or more molar equivalents of acidic alumina with respect to the compound of Formula (I).

In select embodiments, the methods of the present disclosure may produce an amount of exo-tetrahydrocannabinol (exo-THC). In select embodiments, the amount of exo-THC is detectable by HPLC. In select embodiments, the formation of exo-THC may be directly related to the Brønsted-acidity of the catalyst. Exo-THC may have the following structure:

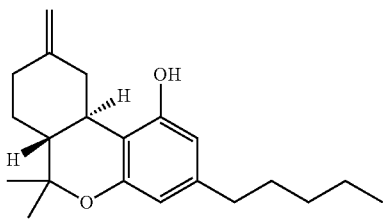 [SMILES: C=C1CC[C@@H]2[C@@H](C1)c1c(O)cc(CCCCC)cc1OC2(C)C]

In select embodiments, the methods of the present disclosure may further comprise a filtering step. By way of non-limiting example the filtering step may employ a fritted Buchner filtering funnel. Suitable filtering apparatus and protocols are within the purview of those skilled in the art.

In select embodiments, the methods of the present disclosure may further comprise a solvent evaporation step, and the solvent evaporation step may be executed under reduced pressure (i.e. in vacuo) for example with a rotary evaporator. Suitable evaporating apparatus and protocols are within the purview of those skilled in the art.

In select embodiments, the methods of the present disclosure may further comprise a step of distillation. Without being bound by any particular theory, distillation may remove impurities and result in a composition comprising a total cannabinoid content about equal to the total cannabinoid content prior to undergoing the methods disclosed herein. Suitable distillation apparatus and protocols are within the purview of those skilled in the art.

EXEMPLARY EMBODIMENTS

The following are non-limiting and exemplary embodiments of the present disclosure:
(1) A method for converting cannabidiol (CBD) into a composition comprising $\Delta^8$-tetrahydrocannabinol ($\Delta^8$-THC) and $\Delta^9$-tetrahydrocannabinol ($\Delta^9$-THC), wherein the composition has a $\Delta^8$-THC:$\Delta^9$-THC ratio that is greater than 1.0:1.0, the method comprising contacting the CBD with a Lewis-acidic heterogeneous reagent under reaction conditions comprising: (i) an aprotic-solvent system; (ii) a reaction temperature that is greater than a threshold reaction temperature for the Lewis-acidic heterogeneous reagent and the aprotic-solvent system; and (iii) a reaction time that is greater than a threshold reaction time for the Lewis-acidic heterogeneous reagent, the aprotic-solvent system, and the reaction temperature.
(2) The method of (1), wherein the Lewis-acidic heterogeneous reagent is a Brønsted-acidic heterogeneous reagent.
(3) The method of (1) or (2), wherein the Lewis-acidic heterogeneous reagent has a Hammett-acidity value ($H_o$) of between about −8.0 and about 0.0.
(4) The method of any one of (1) to (3), wherein the Lewis-acidic heterogeneous reagent has a temperature-programmed desorption value of between about 7.5 and about 0.0 as determined with reference to ammonia ($TPD_{NH3}$).
(5) The method of any one of (1) to (4), wherein the Lewis-acidic heterogeneous reagent has a heat of absorption value of between about −165 and about −100 as determined with reference to ammonia ($\Delta H°_{ads\ NH3}$).
(6) The method of (1), wherein the Lewis-acidic heterogeneous reagent comprises an ion-exchange resin, a microporous silicate, a mesoporous silicate, a phyllosilicate, or a combination thereof.
(7) The method of (6), wherein the ion-exchange resin is an Amberlyst polymeric resin.
(8) The method of (7), wherein the Amberlyst polymeric resin has a surface area of between about 20 m$^2$/g and about 80 m$^2$/g and an average pore diameter of between about 100 Å and about 500 Å.
(9) The method of (7) or (8), wherein the Amberlyst polymeric resin comprises Amberlyst 15.
(10) The method of (6), wherein the ion-exchange resin is a Nafion polymeric resin.
(11) The method of (10), wherein the Nafion polymeric resin comprises NR50, N115, N117, N324, N424, N1110, SAC-13, or a combination thereof.
(12) The method of (6), wherein the Lewis-acidic heterogeneous reagent is Al-MCM-41, MCM-41, MCM-48, SBA-15, SBA-16, ZSM-5, ZSM-11, ZSM-22, ZSM-23, ZSM-35, SAPO-11, SAPO-34, SSZ-13, TS-1, KIT-5, KIT-6, FDU-12, Beta, X-type, Y-type, Linde type A, Linde type L, Linde type X, Linde type Y, Faujasite, Mordenite, Ferrierite, Montmorillonite K10, K30, KSF, Clayzic, bentonite, or a combination thereof.
(13) The method of (12), wherein the acidic heterogeneous reagent has a pore diameter of between about 0.1 nm and about 100 nm, a particle size of between about 0.1 µm and about 50 µm, a Si/Al ratio of between about 5 and about 1500, or a combination thereof.

(14) The method of (12) or (13), wherein the Lewis-acidic heterogeneous reagent is H-ZSM-5, with a Si/Al ratio of about 38, a pore size of about 5 Å, and a particle size of about 2 μm.

(15) The method of (12) or (13), wherein the Lewis-acidic heterogeneous reagent is Na-ZSM-5, with a Si/Al ratio of about 38, a pore size of about 5 Å, and a particle size of about 2 μm.

(16) The method of (12) or (13), wherein the Lewis-acidic heterogeneous reagent is Al-MCM-41 with a Si/Al ratio of about 25, and a pore diameter of about 2.7 nm.

(17) The method of any one of (1) to (16), wherein the aprotic-solvent system comprises a class III solvent.

(18) The method of (17), wherein the class III solvent is heptane.

(19) The method of any one of (1) to (18), wherein prior to being converted to the composition comprising the $\Delta^8$-THC and the $\Delta^9$-THC, the CBD is dissolved in the aprotic-solvent system at a concentration between about 0.001 M and about 2 M.

(20) The method of any one of (1) to (19), wherein the threshold reaction temperature is between about 20° C. and about 100° C.

(21) The method of any one of (1) to (20), wherein the threshold reaction time is between about 10 minutes and about 72 hours.

(22) The method of any one of (1) to (21), wherein the Lewis-acidic heterogeneous reagent has a reagent loading between about 0.1 molar equivalents and about 100 molar equivalents relative to the CBD.

(23) The method of any one of (1) to (22), further comprising isolating the composition from the acidic heterogeneous reagent by a solid-liquid separation technique.

(24) The method of (23), wherein the solid-liquid separation technique comprises filtration, decantation, centrifugation, or a combination thereof.

(25) The method of any one of (1) to (24), wherein the CBD is a component of a distillate, an isolate, a concentrate, an extract, or a combination thereof.

(26) The method of (25), wherein the extract is a crude extract from hemp.

(27) The method of any one of (1) to (26), wherein the $\Delta^8$-THC:$\Delta^9$-THC ratio of the composition is greater than about 3.0:1.0.

(28) The method of any one of (1) to (26), wherein the $\Delta^8$-THC:$\Delta^9$-THC ratio of the composition is greater than about 6.0:1.0.

(29) The method of any one of (1) to (26), wherein the $\Delta^8$-THC:$\Delta^9$-THC ratio of the composition is greater than about 20.0:1.0.

(30) A method for converting cannabidiol (CBD) into $\Delta^8$-tetrahydrocannabinol ($\Delta^8$-THC), the method comprising contacting the CBD with a Lewis-acidic heterogeneous reagent under reaction conditions comprising: (i) an aprotic-solvent system; (ii) a reaction temperature that is greater than a threshold reaction temperature for the Lewis-acidic heterogeneous reagent and the aprotic-solvent system; and (iii) a reaction time that is greater than a threshold reaction time for the Lewis-acidic heterogeneous reagent, the aprotic-solvent system, and the reaction temperature.

(31) The method of (30), wherein the Lewis-acidic heterogeneous reagent is a Brønsted-acidic heterogeneous reagent.

(32) The method of (30) or (31), wherein the Lewis-acidic heterogeneous reagent has a Hammett-acidity value ($H_o$) of between about −8.0 and about 0.0.

(33) The method of any one of (30) to (32), wherein the Lewis-acidic heterogeneous reagent has a temperature-programmed desorption value of between about 7.5 and about 0.0 as determined with reference to ammonia ($TPD_{NH3}$).

(34) The method of any one of (30) to (33), wherein the Lewis-acidic heterogeneous reagent has a heat of absorption value of between about −165 and about −100 as determined with reference to ammonia ($\Delta H^\circ_{ads\ NH3}$).

(35) The method of (30), wherein the Lewis-acidic heterogeneous reagent comprises an ion-exchange resin, a microporous silicate, a mesoporous silicate, a phyllosilicate, or a combination thereof.

(36) The method of (35), wherein the ion-exchange resin is an Amberlyst polymeric resin.

(37) The method of (36), wherein the Amberlyst polymeric resin has a surface area of between about 20 m$^2$/g and about 80 m$^2$/g and an average pore diameter of between about 100 Å and about 500 Å.

(38) The method of (36) or (37), wherein the Amberlyst polymeric resin comprises Amberlyst 15.

(39) The method of (35), wherein the ion-exchange resin is a Nafion polymeric resin.

(40) The method of (39), wherein the Nafion polymeric resin comprises NR50, N115, N117, N324, N424, N1110, SAC-13, or a combination thereof.

(41) The method of (35), wherein the Lewis-acidic heterogeneous reagent is Al-MCM-41, MCM-41, MCM-48, SBA-15, SBA-16, ZSM-5, ZSM-11, ZSM-22, ZSM-23, ZSM-35, SAPO-11, SAPO-34, SSZ-13, TS-1, KIT-5, KIT-6, FDU-12, Beta, X-type, Y-type, Linde type A, Linde type L, Linde type X, Linde type Y, Faujasite, Mordenite, Ferrierite, Montmorillonite K10, K30, KSF, Clayzic, bentonite, or a combination thereof.

(42) The method of (41), wherein the acidic heterogeneous reagent has a pore diameter of between about 0.1 nm and about 100 nm, a particle size of between about 0.1 μm and about 50 μm, a Si/Al ratio of between about 5 and about 1500, or a combination thereof.

(43) The method of (41) or (42), wherein the Lewis-acidic heterogeneous reagent is H-ZSM-5, with a Si/Al ratio of about 38, a pore size of about 5 Å, and a particle size of about 2 μm.

(44) The method of (41) or (42), wherein the Lewis-acidic heterogeneous reagent is Na-ZSM-5, with a Si/Al ratio of about 38, a pore size of about 5 Å, and a particle size of about 2 μm.

(45) The method of (41) or (42), wherein the Lewis-acidic heterogeneous reagent is Al-MCM-41 with a Si/Al ratio of about 25, and a pore diameter of about 2.36 nm.

(46) The method of any one of (30) to (35), wherein the aprotic-solvent system comprises a class III solvent.

(47) The method of (46), wherein the class III solvent is heptane.

(48) The method of any one of (30) to (47), wherein prior to being converted to the $\Delta^8$-THC, the CBD is dissolved in the aprotic-solvent system at a concentration between about 0.001 M and about 2 M.

(49) The method of any one of (30) to (48), wherein the threshold reaction temperature is between about 20° C. and about 100° C.

(50) The method of any one of (30) to (49), wherein the threshold reaction time is between about 10 minutes and about 36 hours.

(51) The method of any one of (30) to (50), wherein the Lewis-acidic heterogeneous reagent has a reagent loading between about 0.1 molar equivalents and about 100 molar equivalents relative to the CBD.

(52) The method of any one of (30) to (51), further comprising isolating the composition from the acidic heterogeneous reagent by a solid-liquid separation technique.

(53) The method of (52), wherein the solid-liquid separation technique comprises filtration, decantation, centrifugation, or a combination thereof.

(54) The method of any one of (30) to (53), wherein the CBD is a component of a distillate, an isolate, a concentrate, an extract, or a combination thereof.

(55) The method of (54), wherein the extract is a crude extract from hemp.

(56) A method for converting cannabidiol (CBD) into a composition comprising $\Delta^8$-tetrahydrocannabinol ($\Delta^8$-THC) and $\Delta^9$-tetrahydrocannabinol ($\Delta^9$-THC), wherein the composition has a $\Delta^8$-THC:$\Delta^9$-THC ratio that is greater than 1.0:1.0, the method comprising contacting the CBD with a Lewis-acidic heterogeneous reagent under neat reaction conditions comprising: (i) a reaction temperature that is greater than a threshold reaction temperature for the Lewis-acidic heterogeneous reagent; and (ii) a reaction time that is greater than a threshold reaction time for the Lewis-acidic heterogeneous reagent and the reaction temperature.

(57) The method of (56), wherein the Lewis-acidic heterogeneous reagent is a Brønsted-acidic heterogeneous reagent.

(58) The method of (56) or (57), wherein the Lewis-acidic heterogeneous reagent has a Hammett-acidity value ($H_o$) of between about −8.0 and about 0.0.

(59) The method of any one of (56) to (58), wherein the Lewis-acidic heterogeneous reagent has a temperature-programmed desorption value of between about 7.5 and about 0.0 as determined with reference to ammonia ($TPD_{NH3}$).

(60) The method of any one of (56) to (59), wherein the Lewis-acidic heterogeneous reagent has a heat of absorption value of between about −165 and about −100 as determined with reference to ammonia ($\Delta H°_{ads\ NH3}$).

(61) The method of (56), wherein the Lewis-acidic heterogeneous reagent comprises ion-exchange resin, a microporous silicate, a mesoporous silicate, a phyllosilicate, or a combination thereof.

(62) The method of (61), wherein the ion-exchange resin is an Amberlyst polymeric resin.

(63) The method of (62), wherein the Amberlyst polymeric resin has a surface area of between about 20 $m^2/g$ and about 80 $m^2/g$ and an average pore diameter of between about 100 Å and about 500 Å.

(64) The method of (62) or (63), wherein the Amberlyst polymeric resin comprises Amberlyst 15.

(65) The method of (61), wherein the ion-exchange resin is a Nafion polymeric resin.

(66) The method of (65), wherein the Nafion polymeric resin comprises NR50, N115, N117, N324, N424, N1110, SAC-13, or a combination thereof.

(67) The method of (61), wherein the Lewis-acidic heterogeneous reagent is Al-MCM-41, MCM-41, MCM-48, SBA-15, SBA-16, ZSM-5, ZSM-11, ZSM-22, ZSM-23, ZSM-35, SAPO-11, SAPO-34, SSZ-13, TS-1, KIT-5, KIT-6, FDU-12, Beta, X-type, Y-type, Linde type A, Linde type L, Linde type X, Linde type Y, Faujasite, Mordenite, Ferrierite, Montmorillonite K10, K30, KSF, Clayzic, bentonite, or a combination thereof.

(68) The method of (67), wherein the acidic heterogeneous reagent has a pore diameter of between about 0.1 nm and about 100 nm, a particle size of between about 0.1 μm and about 50 μm, a Si/Al ratio of between about 5 and about 1500, or a combination thereof.

(69) The method of (67) or (68), wherein the Lewis-acidic heterogeneous reagent is H-ZSM-5, with a Si/Al ratio of about 38, a pore size of about 5 Å, and a particle size of about 2 μm.

(70) The method of (67) or (68), wherein the Lewis-acidic heterogeneous reagent is Na-ZSM-5, with a Si/Al ratio of about 38, a pore size of about 5 Å, and a particle size of about 2 μm.

(71) The method of (67) or (68), wherein the Lewis-acidic heterogeneous reagent is Al-MCM-41 with a Si/Al ratio of about 25, and a pore diameter of about 2.7 nm.

(72) The method of any one of (56) to (71), wherein the threshold reaction temperature is between about 20° C. and about 100° C.

(73) The method of any one of (56) to (72), wherein the threshold reaction time is between about 10 minutes and about 72 hours.

(74) The method of any one of (56) to (73), wherein the Lewis-acidic heterogeneous reagent has a reagent loading between about 0.1 molar equivalents and about 100 molar equivalents relative to the CBD.

(75) The method of any one of (56) to (74), wherein the CBD is a component of a distillate, an isolate, a concentrate, an extract, or a combination thereof.

(76) The method of (75), wherein the extract is a crude extract from hemp.

(77) The method of any one of (56) to (76), wherein the $\Delta^8$-THC:$\Delta^9$-THC ratio of the composition is greater than about 3.0:1.0.

(78) The method of any one of (56) to (76), wherein the $\Delta^8$-THC:$\Delta^9$-THC ratio of the composition is greater than about 6.0:1.0.

(79) The method of any one of (56) to (76), wherein the $\Delta^8$-THC:$\Delta^9$-THC ratio of the composition is greater than about 20.0:1.0.

(80) A method for converting cannabidiol (CBD) into $\Delta^8$-tetrahydrocannabinol ($\Delta^8$-THC), the method comprising contacting the CBD with a Lewis-acidic heterogeneous reagent under neat reaction conditions comprising: (i) a reaction temperature that is greater than a threshold reaction temperature for the Lewis-acidic heterogeneous reagent; and (ii) a reaction time that is greater than a threshold reaction time for the Lewis-acidic heterogeneous reagent and the reaction temperature.

(81) The method of (80), wherein the Lewis-acidic heterogeneous reagent is a Brønsted-acidic heterogeneous reagent.

(82) The method of (80) or (81), wherein the Lewis-acidic heterogeneous reagent has a Hammett-acidity value ($H_o$) of between about −8.0 and about 0.0.

(83) The method of any one of (80) to (82), wherein the Lewis-acidic heterogeneous reagent has a temperature-programmed desorption value of between about 7.5 and about 0.0 as determined with reference to ammonia ($TPD_{NH3}$).

(84) The method of any one of (80) to (83), wherein the Lewis-acidic heterogeneous reagent has a heat of absorption value of between about −165 and about −100 as determined with reference to ammonia ($\Delta H°_{ads\ NH3}$).
(85) The method of (80), wherein the Lewis-acidic heterogeneous reagent comprises an ion-exchange resin, a microporous silicate, a mesoporous silicate, a phyllosilicate, or a combination thereof.
(86) The method of (85), wherein the ion-exchange resin is an Amberlyst polymeric resin.
(87) The method of (86), wherein the Amberlyst polymeric resin has a surface area of between about 20 m²/g and about 80 m²/g and an average pore diameter of between about 100 Å and about 500 Å.
(88) The method of (86) or (87), wherein the Amberlyst polymeric resin comprises Amberlyst 15.
(89) The method of (85), wherein the ion-exchange resin is a Nafion polymeric resin.
(90) The method of (89), wherein the Nafion polymeric resin comprises NR50, N115, N117, N324, N424, N1110, SAC-13, or a combination thereof.
(91) The method of (85), wherein the Lewis-acidic heterogeneous reagent is Al-MCM-41, MCM-41, MCM-48, SBA-15, SBA-16, ZSM-5, ZSM-11, ZSM-22, ZSM-23, ZSM-35, SAPO-11, SAPO-34, SSZ-13, TS-1, KIT-5, KIT-6, FDU-12, Beta, X-type, Y-type, Linde type A, Linde type L, Linde type X, Linde type Y, Faujasite, Mordenite, Ferrierite, Montmorillonite K10, K30, KSF, Clayzic, bentonite, or a combination thereof.
(92) The method of (91), wherein the acidic heterogeneous reagent has a pore diameter of between about 0.1 nm and about 100 nm, a particle size of between about 0.1 μm and about 50 μm, a Si/Al ratio of between about 5 and about 1500, or a combination thereof.
(93) The method of (91) or (92), wherein the Lewis-acidic heterogeneous reagent is H-ZSM-5, with a Si/Al ratio of about 38, a pore size of about 5 Å, and a particle size of about 2 μm.
(94) The method of (91) or (92), wherein the Lewis-acidic heterogeneous reagent is Na-ZSM-5, with a Si/Al ratio of about 38, a pore size of about 5 Å, and a particle size of about 2 μm.
(95) The method of (91) or (92), wherein the Lewis-acidic heterogeneous reagent is Al-MCM-41 with a Si/Al ratio of about 25, and a pore diameter of about 2.7 nm.
(96) The method of any one of (80) to (95), wherein the threshold reaction temperature is between about 20° C. and about 100° C.
(97) The method of any one of (80) to (96), wherein the threshold reaction time is between about 10 minutes and about 72 hours.
(98) The method of any one of (80) to (97), wherein the Lewis-acidic heterogeneous reagent has a reagent loading between about 0.1 molar equivalents and about 100 molar equivalents relative to the CBD.
(99) The method of any one of (80) to (98), wherein the CBD is a component of a distillate, an isolate, a concentrate, an extract, or a combination thereof.
(100) The method of (99), wherein the extract is a crude extract from hemp.
(101) A method for converting CBD into a composition comprising $\Delta^8$-THC and $\Delta^9$-THC, wherein the composition has a $\Delta^8$-THC:$\Delta^9$-THC ratio that is greater than 1.0:1.0, the method comprising contacting the CBD with a Lewis-acidic heterogeneous reagent under reaction conditions comprising: (i) a protic-solvent system; (ii) a reaction temperature that is greater than a threshold reaction temperature for the Lewis-acidic heterogeneous reagent and the protic-solvent system; and (iii) a reaction time that is greater than a threshold reaction time for the Lewis-acidic heterogeneous reagent, the protic-solvent system, and the reaction temperature.
(102) The method of (101), wherein the Lewis-acidic heterogeneous reagent is a Brønsted-acidic heterogeneous reagent.
(103) The method of (101) or (102), wherein the Lewis-acidic heterogeneous reagent has a Hammett-acidity value ($H_o$) of between about −8.0 and about 0.0.
(104) The method of any one of (101) to (103), wherein the Lewis-acidic heterogeneous reagent has a temperature-programmed desorption value of between about 7.5 and about 0.0 as determined with reference to ammonia ($TPD_{NH3}$).
(105) The method of any one of (101) to (104), wherein the Lewis-acidic heterogeneous reagent has a heat of absorption value of between about −165 and about −100 as determined with reference to ammonia ($\Delta H°_{ads\ NH3}$).
(106) The method of (101), wherein the Lewis-acidic heterogeneous reagent comprises an ion-exchange resin, a microporous silicate, a mesoporous silicate, a phyllosilicate, or a combination thereof.
(107) The method of (106), wherein the ion-exchange resin is an Amberlyst polymeric resin.
(108) The method of (107), wherein the Amberlyst polymeric resin has a surface area of between about 20 m²/g and about 80 m²/g and an average pore diameter of between about 100 Å and about 500 Å.
(109) The method of (107) or (108), wherein the Amberlyst polymeric resin comprises Amberlyst 15.
(110) The method of (106), wherein the ion-exchange resin is a Nafion polymeric resin.
(111) The method of (110), wherein the Nafion polymeric resin comprises NR50, N115, N117, N324, N424, N1110, SAC-13, or a combination thereof.
(112) The method of (106), wherein the Lewis-acidic heterogeneous reagent is Al-MCM-41, MCM-41, MCM-48, SBA-15, SBA-16, ZSM-5, ZSM-11, ZSM-22, ZSM-23, ZSM-35, SAPO-11, SAPO-34, SSZ-13, TS-1, KIT-5, KIT-6, FDU-12, Beta, X-type, Y-type, Linde type A, Linde type L, Linde type X, Linde type Y, Faujasite, Mordenite, Ferrierite, Montmorillonite K10, K30, KSF, Clayzic, bentonite, or a combination thereof.
(113) The method of (112), wherein the acidic heterogeneous reagent has a pore diameter of between about 0.1 nm and about 100 nm, a particle size of between about 0.1 μm and about 50 μm, a Si/Al ratio of between about 5 and about 1500, or a combination thereof.
(114) The method of (112) or (113), wherein the Lewis-acidic heterogeneous reagent is H-ZSM-5, with a Si/Al ratio of about 38, a pore size of about 5 Å, and a particle size of about 2 μm.
(115) The method of (112) or (113), wherein the Lewis-acidic heterogeneous reagent is Na-ZSM-5, with a Si/Al ratio of about 38, a pore size of about 5 Å, and a particle size of about 2 μm.
(116) The method of (112) or (113), wherein the Lewis-acidic heterogeneous reagent is Al-MCM-41 with a Si/Al ratio of about 25, and a pore diameter of about 2.7 nm.

(117) The method of any one of (101) to (116), wherein the protic-solvent system comprises a class III solvent.
(118) The method of (117), wherein the class III solvent is ethanol.
(119) The method of any one of (101) to (118), wherein prior to being converted to the composition comprising the $\Delta^8$-THC and the $\Delta^9$-THC, the CBD is dissolved in the protic-solvent system at a concentration between about 0.001 M and about 2 M.
(120) The method of any one of (101) to (119), wherein the threshold reaction temperature is between about 20° C. and about 100° C.
(121) The method of any one of (101) to (120), wherein the threshold reaction time is between about 10 minutes and about 72 hours.
(122) The method of any one of (101) to (121), wherein the Lewis-acidic heterogeneous reagent has a reagent loading between about 0.1 molar equivalents and about 100 molar equivalents relative to the CBD.
(123) The method of any one of (101) to (122), further comprising isolating the composition from the acidic heterogeneous reagent by a solid-liquid separation technique.
(124) The method of (123), wherein the solid-liquid separation technique comprises filtration, decantation, centrifugation, or a combination thereof.
(125) The method of any one of (101) to (124), wherein the CBD is a component of a distillate, an isolate, a concentrate, an extract, or a combination thereof.
(126) The method of (125), wherein the extract is a crude extract from hemp.
(127) The method of any one of (101) to (126), wherein the $\Delta^8$-THC:$\Delta^9$-THC ratio of the composition is greater than about 3.0:1.0.
(128) The method of any one of (101) to (126), wherein the $\Delta^8$-THC:$\Delta^9$-THC ratio of the composition is greater than about 6.0:1.0.
(129) The method of any one of (101) to (126), wherein the $\Delta^8$-THC:$\Delta^9$-THC ratio of the composition is greater than about 20.0:1.0.
(130) A method for converting CBD into $\Delta^8$-THC, the method comprising contacting the CBD with a Lewis-acidic heterogeneous reagent under reaction conditions comprising: (i) a protic-solvent system; (ii) a reaction temperature that is greater than a threshold reaction temperature for the Lewis-acidic heterogeneous reagent and the protic-solvent system; and (iii) a reaction time that is greater than a threshold reaction time for the Lewis-acidic heterogeneous reagent, the protic-solvent system, and the reaction temperature.
(131) The method of (130), wherein the Lewis-acidic heterogeneous reagent is a Brønsted-acidic heterogeneous reagent.
(132) The method of (130) or (131), wherein the Lewis-acidic heterogeneous reagent has a Hammett-acidity value ($H_o$) of between about −8.0 and about 0.0.
(133) The method of any one of (130) to (132), wherein the Lewis-acidic heterogeneous reagent has a temperature-programmed desorption value of between about 7.5 and about 0.0 as determined with reference to ammonia ($TPD_{NH3}$).
(134) The method of any one of (130) to (133), wherein the Lewis-acidic heterogeneous reagent has a heat of absorption value of between about −165 and about −100 as determined with reference to ammonia ($\Delta H°_{ads\ NH3}$).
(135) The method of (1), wherein the Lewis-acidic heterogeneous reagent comprises an ion-exchange resin, a microporous silicate, a mesoporous silicate, a phyllosilicate, or a combination thereof.
(136) The method of (135), wherein the ion-exchange resin is an Amberlyst polymeric resin.
(137) The method of (136), wherein the Amberlyst polymeric resin has a surface area of between about 20 m$^2$/g and about 80 m$^2$/g and an average pore diameter of between about 100 Å and about 500 Å.
(138) The method of (136) or (137), wherein the Amberlyst polymeric resin comprises Amberlyst 15.
(139) The method of (135), wherein the ion-exchange resin is a Nafion polymeric resin.
(140) The method of (139), wherein the Nafion polymeric resin comprises NR50, N115, N117, N324, N424, N1110, SAC-13, or a combination thereof.
(141) The method of (135), wherein the Lewis-acidic heterogeneous reagent is Al-MCM-41, MCM-41, MCM-48, SBA-15, SBA-16, ZSM-5, ZSM-11, ZSM-22, ZSM-23, ZSM-35, SAPO-11, SAPO-34, SSZ-13, TS-1, KIT-5, KIT-6, FDU-12, Beta, X-type, Y-type, Linde type A, Linde type L, Linde type X, Linde type Y, Faujasite, Mordenite, Ferrierite, Montmorillonite K10, K30, KSF, Clayzic, bentonite, or a combination thereof.
(142) The method of (141), wherein the acidic heterogeneous reagent has a pore diameter of between about 0.1 nm and about 100 nm, a particle size of between about 0.1 μm and about 50 μm, a Si/Al ratio of between about 5 and about 1500, or a combination thereof.
(143) The method of (141) or (142), wherein the Lewis-acidic heterogeneous reagent is H-ZSM-5, with a Si/Al ratio of about 38, a pore size of about 5 Å, and a particle size of about 2 μm.
(144) The method of (141) or (142), wherein the Lewis-acidic heterogeneous reagent is Na-ZSM-5, with a Si/Al ratio of about 38, a pore size of about 5 Å, and a particle size of about 2 μm.
(145) The method of (141) or (142), wherein the Lewis-acidic heterogeneous reagent is Al-MCM-41 with a Si/Al ratio of about 25, and a pore diameter of about 2.7 nm.
(146) The method of any one of (130) to (145), wherein the protic-solvent system comprises a class III solvent.
(147) The method of (146), wherein the class III solvent is ethanol.
(148) The method of any one of (130) to (147), wherein prior to being converted to the $\Delta^8$-THC, the CBD is dissolved in the protic-solvent system at a concentration between about 0.001 M and about 2 M.
(149) The method of any one of (130) to (148), wherein the threshold reaction temperature is between about 20° C. and about 100° C.
(150) The method of any one of (130) to (149), wherein the threshold reaction time is between about 10 minutes and about 72 hours.
(151) The method of any one of (130) to (150), wherein the Lewis-acidic heterogeneous reagent has a reagent loading between about 0.1 molar equivalents and about 100 molar equivalents relative to the CBD.
(152) The method of any one of 130) to (151), further comprising isolating the composition from the acidic heterogeneous reagent by a solid-liquid separation technique.

(153) The method of (152), wherein the solid-liquid separation technique comprises filtration, decantation, centrifugation, or a combination thereof.

(154) The method of any one of (130) to (153), wherein the CBD is a component of a distillate, an isolate, a concentrate, an extract, or a combination thereof.

(155) The method of (154), wherein the extract is a crude extract from hemp.

(156) A method for converting CBD into $\Delta^8$-THC, the method comprising contacting the CBD with an ion-exchange resin under reaction conditions comprising: (i) a class III solvent; (ii) a reaction temperature that is greater than about 60° C.; and (iii) a reaction time that is greater than about 60 minutes.

(157) A method for converting CBD into a composition comprising $\Delta^8$-THC and $\Delta^9$-THC, wherein the composition has a $\Delta^8$-THC:$\Delta^9$-THC ratio that is greater than 1.0:1.0, the method comprising contacting the CBD with an aluminosilicate-based reagent under reaction conditions comprising: (i) a class III solvent; (ii) a reaction temperature that is greater than about 70° C.; and (iii) a reaction time that is greater than about 60 minutes.

(158) A method for converting cannabidiol (CBD) into $\Delta^8$-tetrahydrocannabinol ($\Delta^8$-THC), the method comprising heating CBD and a Lewis-acidic heterogeneous reagent in an aprotic-solvent system, wherein the Lewis-acidic heterogeneous reagent is acidic alumina.

(159) The method of (158), wherein thy: heating step occurs at a temperature in a range from about 80° C. to about 110° C.

(160) The method of (158), wherein the heating step occurs at a temperature in a range from about 80° C. to about 100° C.

(161) The method of (158), wherein the heating step occurs at a temperature in a range from about 80° C. to about 95° C.

(162) The method of any one of (158) to (161), wherein the heating step occurs in an inert atmosphere.

(163) The method of any one of (158) to (162), wherein the heating step is performed in a stirred tank reactor or a rotary bed reactor.

(164) The method of any one of (158) to (163), wherein the Lewis-acidic heterogeneous reagent is in an amount of between about 0.1 to about 100 molar equivalents with respect to CBD.

(165) The method of any one of (158) to (163), wherein the Lewis-acidic heterogeneous reagent is in an amount of between about 1 to about 50 molar equivalents with respect to CBD.

(166) The method of any one of (158) to (163), wherein the Lewis-acidic heterogeneous reagent s in an amount of between about 1 to about 25 molar equivalents with respect to CBD.

(167) The method of any one of (158) to (163), wherein the Lewis-acidic heterogeneous reagent is in an amount of between about 1 to about 10 molar equivalents with respect to CBD.

(168) The method of any one of (158) to (163), wherein the Lewis-acidic heterogeneous reagent is in an amount of between about 1 to about 5 molar equivalents with respect to CBD.

(169) The method of any one of (158) to (168), wherein the aprotic-solvent system comprises acetone, dimethyl sulfoxide, ethyl acetate, dichloromethane, chloroform, toluene, pentane, heptane, hexane, diethyl ether, tert-butyl methyl ether, tetrahydrofuran, dioxane, dimethylformamide, dimethylacetamide, N-methylpyrrolidone, anisole, butyl acetate, cumene, ethyl formate, isobutyl acetate, isopropyl acetate, methyl acetate, methylethylketone, methylisobutylketone, propyl acetate, cyclohexane, para-xylene, meta-xylene, ortho-xylene, 1,2-dichloroethane, or any combination thereof.

(170) The method of any one of (158) to (168), wherein the aprotic-solvent system is heptane.

(171) The method of any one of (158) to (169), further comprising drying the acidic alumina before the heating step.

(172) A method for converting cannabidiol (CBD) into $\Delta^8$-tetrahydrocannabinol ($\Delta^8$-THC), the method comprising heating CBD and a Lewis-acidic heterogeneous reagent in an aprotic-solvent system at a temperature in a range from about 80° C. to about 110° C., and wherein the Lewis-acidic heterogeneous reagent is acidic alumina and is in an amount of between about 1 to about 100 molar equivalents with respect to CBD.

(173) The method of (172), wherein the heating step occurs in an inert atmosphere.

(174) The method of (172) or (173), wherein the heating step is performed in a stirred tank reactor or a rotary bed reactor.

(175) The method of any one of (172) to (174), wherein the Lewis-acidic heterogeneous reagent is in an amount of between about 1 to about 10 molar equivalents with respect to CBD.

(176) The method of any one of (172) to (175), wherein the aprotic-solvent system comprises acetone, dimethyl sulfoxide, ethyl acetate, dichloromethane, chloroform, toluene, pentane, heptane, hexane, diethyl ether, tert-butyl methyl ether, tetrahydrofuran, dioxane, dimethylformamide, dimethylacetamide, N-methylpyrrolidone, anisole, butyl acetate, cumene, ethyl formate, isobutyl acetate, isopropyl acetate, methyl acetate, methylethylketone, methylisobutylketone, propyl acetate, cyclohexane, para-xylene, meta-xylene, ortho-xylene, 1,2-dichloroethane, or any combination thereof.

(177) The method of any one of (172) to (175), wherein the aprotic-solvent system is heptane.

(178) A method for converting a compound of Formula (I) into a compound of Formula (II), the method comprising heating a compound of Formula (I)

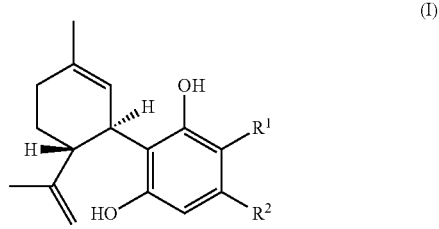

and a Lewis-acidic heterogeneous reagent in an aprotic-solvent system to provide a compound of Formula (II)

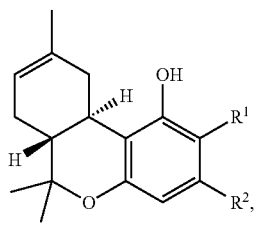

(II)

wherein the Lewis-acidic heterogeneous reagent is acidic alumina, and wherein $R^1$ is hydrogen or COOH, and $R^2$ is hydrogen, $C_1$-$C_{12}$ alkyl, $C_2$-$C_{12}$ alkenyl, $C_2$-$C_{12}$ alkynyl, $(OCH_2CH_2)_{0-6}O(C_1$-$C_8$ alkyl), $(C_0$-$C_4$ alkyl)-$NR^{2a}R^{2b}$, $(C_0$-$C_4$ alkyl)-aryl, $(C_0$-$C_4$ alkyl)-heteroaryl, $(C_0$-$C_4$ alkyl)-cycloalkyl, or $(C_0$-$C_4$ alkyl)-heterocycloalkyl, wherein $R^{2a}R^{2b}$ are each independently hydrogen or $C_1$-$C_6$ alkyl.

(179) The method of (178), wherein the heating step occurs at a temperature in a range from about 80° C. to about 110° C.

(180) The method of (178), wherein the heating step occurs at a temperature in a range from about 80° C. to about 100° C.

(181) The method of (178), wherein the heating step occurs at a temperature in a range from about 80° C. to about 95° C.

(182) The method of any one of (178) (181), wherein the heating step occurs in an inert atmosphere.

(183) The method of any one of (178) to (182), wherein the heating step is performed in a stirred tank reactor or a rotary bed reactor.

(184) The method of any one of (178) to (183), wherein the compound of Formula (I) is a component of a distillate, an isolate, a concentrate or an extract.

(185) The method of any one of (178) to (184), wherein the Lewis-acidic heterogeneous reagent is in an amount of between about 0.1 to about 100 molar equivalents with respect to the compound of Formula (I).

(186) The method of any one of (178) to (184), wherein the Lewis-acidic heterogeneous reagent is in an amount of between about 1 to about 50 molar equivalents with respect to the compound of Formula (I).

(187) The method of any one of (178) to (184), wherein the Lewis-acidic heterogeneous reagent is in an amount of between about 1 to about 25 molar equivalents with respect to the compound of Formula (I).

(188) The method of any one of (178) to (184), wherein the Lewis-acidic heterogeneous reagent is in an amount of between about 1 to about 10 molar equivalents with respect to the compound of Formula (I).

(189) The method of any one of (178) to (184), wherein the Lewis-acidic heterogeneous reagent is in an amount of between about 1 to about 5 molar equivalents with respect to the compound of Formula (I).

(190) The method of any one of (178) to (189), wherein the aprotic-solvent system comprises acetone, dimethyl sulfoxide, ethyl acetate, dichloromethane, chloroform, toluene, pentane, heptane, hexane, diethyl ether, tert-butyl methyl ether, tetrahydrofuran, dioxane, dimethylformamide, dimethylacetamide, N-methylpyrrolidone, anisole, butyl acetate, cumene, ethyl formate, isobutyl acetate, isopropyl acetate, methyl acetate, methylethylketone, methylisobutylketone, propyl acetate, cyclohexane, para-xylene, meta-xylene, ortho-xylene, 1,2-dichloroethane, or any combination thereof.

(191) The method of any one of (78) to (189), wherein the aprotic-solvent system is heptane.

(192) The method of any one of (178) to (191), further comprising drying the acidic alumina before the heating step.

(193) The method of any one of (178) to (192), wherein $R^1$ is hydrogen.

(194) The method of any one of (178) to (192), wherein $R^1$ is COOH.

(195) The method of any one of (178) to (194), wherein $R^2$ is $C_3H_7$.

(196) The method of any one of (178) to (195), wherein $R^2$ is $C_5H_{11}$.

(197) The method of any one of (178) to (195), wherein $R^2$ is $C_7H_{15}$.

(198) The method of any one of (178) to (192), wherein the compound of Formula (I) is cannabidiol (CBD) and the compound of Formula (II) is $\Delta^8$-tetrahydrocannabinol ($\Delta^8$-THC).

(199) The method of any one of (178) to (192), wherein the compound of Formula (I) is cannabidiolic acid (CBDA) and the compound of Formula (II) is $\Delta^8$-tetrahydrocannabinolic acid ($\Delta^8$-THCA).

(200) A method for converting a compound of Formula (I) into a compound of Formula (II), the method comprising contacting a compound of Formula (I)

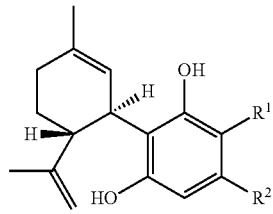

(I)

with a Lewis-acidic heterogeneous reagent, optionally in an aprotic-solvent system, to provide a compound of Formula (II)

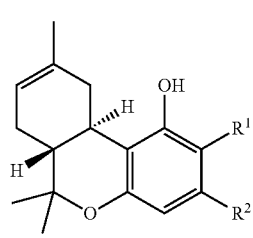

(II)

wherein the Lewis-acidic heterogeneous reagent comprises an ion-exchange resin, a microporous silicate, a mesoporous silicate, a phyllosilicate, or a combination thereof; wherein $R^1$ is hydrogen or COOH, and $R^2$ is hydrogen, $C_1$-$C_{12}$ alkyl, $C_2$-$C_{12}$ alkenyl, $C_2$-$C_{12}$ alkynyl, $(OCH_2CH_2)_{0-6}O(C_1$-$C_8$ alkyl), $(C_0$-$C_4$ alkyl)-$NR^{2a}R^{2b}$, $(C_0$-$C_4$ alkyl)-aryl, $(C_0$-$C_4$ alkyl)-heteroaryl, $(C_0$-$C_4$ alkyl)-cycloalkyl, or $(C_0$-$C_4$ alkyl)-heterocycloalkyl, wherein $R^{2a}R^{2b}$ are each independently hydrogen or $C_1$-$C_6$ alkyl; and wherein the compound of Formula (I) is other than cannabidiol (CBD) and the compound of Formula (II) is other than $\Delta^8$-tetrahydrocannabinol ($\Delta^8$-THC).

(201) The method of (200), wherein the Lewis-acidic heterogeneous reagent is the ion-exchange resin and is an Amberlyst polymeric resin which is Amberlyst-15, 16, 31, 33, 35, 36, 39, 46, 70, CH10, CH28, CH43 or M-31, or a H⁺ or Na⁺ form thereof, or any combination thereof.

(202) The method of (200), wherein the Lewis-acidic heterogeneous reagent is the ion-exchange resin and is a Nafion polymeric resin which is Nafion-NR50, N115, N117, N324, N424 or N1110, SAC-13, or a H⁺ or Na⁺ form thereof, or any combination thereof.

(203) The method of (200), wherein the Lewis-acidic heterogeneous reagent is the ion-exchange resin and is other than Amberlyst-15 or Nafion-SAC-13.

(204) The method of any one of (200) to (203), further comprising heating the compound of Formula (I), the Lewis-acidic heterogeneous reagent and the aprotic-solvent system.

(205) The method of (204), wherein the heating is at greater than about 60° C.

(206) The method of (200), wherein the Lewis-acidic heterogeneous reagent is the microporous silicate and is a zeolite which is ZSM-5, ZSM-11, ZSM-22, ZSM-23, ZSM-35, SAPO-11, SAPO-34, SSZ-13, TS-1, Beta, X-type, Y-type, Linde type A, Linde type L, Linde type X, or Linde type Y, or a H+ or Na+ form thereof, or any combination thereof.

(207) The method of (200), wherein the Lewis-acidic heterogeneous reagent is the microporous silicate and is other than Zeolite Y, Zeolite Beta, or SAPO-11.

(208) The method of (206) or (207), further comprising heating the compound of Formula (I), the Lewis-acidic heterogeneous reagent and the aprotic-solvent system.

(209) The method of (208), wherein the heating is at greater than about 70° C.

(210) The method of (200), wherein the Lewis-acidic heterogeneous reagent is the mesoporous silicate and is Al-MCM-41, MCM-41, MCM-48, SBA-15, SBA-16, KIT-5, KIT-6, FDU-12, or any combination thereof.

(211) The method of (210), further comprising heating the compound of Formula (I), the Lewis-acidic heterogeneous reagent and aprotic-solvent system.

(212) The method of (211), wherein the heating is at greater than about 70° C.

(213) The method of (200), wherein the Lewis-acidic heterogeneous reagent is the phyllosilicate and is Faujasite, Mordenite, Ferrierite, Montmorillonite K10, Montmorillonite K20, Montmorillonite K30, Montmorillonite KSF, Clayzic, bentonite, or any combination thereof.

(214) The method of (213), wherein the phyllosilicate is Montmorillonite K10, Montmorillonite K20, Montmorillonite K30 or Montmorillonite KSF.

(215) The method of (213) or (214), further comprising heating the compound of Formula (I), the Lewis-acidic heterogeneous reagent and the aprotic-solvent system.

(216) The method of (215), wherein the heating is at greater than about 60° C.

(217) The method of any one of (200) to (216), wherein the contacting step is under neat conditions.

(218) The method of any one of (200) to (216), wherein the aprotic-solvent system is present.

(219) The method of (218), wherein the aprotic-solvent system comprises acetone, dimethyl sulfoxide, ethyl acetate, dichloromethane, chloroform, toluene, pentane, heptane, hexane, diethyl ether, tert-butyl methyl ether, tetrahydrofuran, dioxane, dimethylformamide, dimethylacetamide, N-methylpyrrolidone, anisole, butyl acetate, cumene, ethyl formate, isobutyl acetate, isopropyl acetate, methyl acetate, methylethylketone, methylisobutylketone, propyl acetate, cyclohexane, para-xylene, meta-xylene, ortho-xylene, 1,2-dichloroethane, or any combination thereof.

(219) The method of (218), wherein the aprotic-solvent system is heptane.

(220) The method of any one of (200) to (219), wherein the compound of Formula (II) is a component of a composition that further comprises a compound of Formula (III)

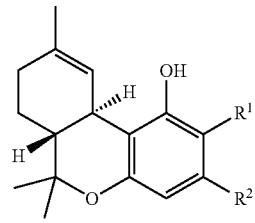

(III)

and wherein the composition has a compound of Formula (II):compound of Formula (III) ratio that is greater than 1.0:1.0.

(221) The method of any one of (200) to (220), wherein $R^1$ is COOH.

(222) The method of any one of (200) to (220), wherein $R^1$ is hydrogen.

(223) The method of any one of (200) to (221), wherein $R^2$ is $C_5H_{11}$.

(224) The method of any one of (200) to (222), wherein $R^2$ is $C_3H_7$.

(225) The method of any one of (200) to (222), wherein $R^2$ is $C_7H_{15}$.

(226) The method of any one of (200) to (215), wherein the compound of Formula (I) is cannabidiolic acid (CBDA) and the compound of Formula (II) is $\Delta^8$-tetrahydrocannabinolic acid ($\Delta^8$-THCA).

EXAMPLES

EXAMPLE 1: To a solution of CBD (500 mg, 1.59 mmol) in heptane (10 mL) was added Amberlyst-15 (100 mg). The reaction was stirred at room temperature for 24 hours. The reaction was filtered using a fritted Buchner filtering funnel and then the reaction solvent was evaporated in vacuo. Analysis by HPLC showed near complete consumption of CBD (<1% remained) with $\Delta^8$-THC as the major product (see, TABLE 2 and FIG. 1).

Figure 2:
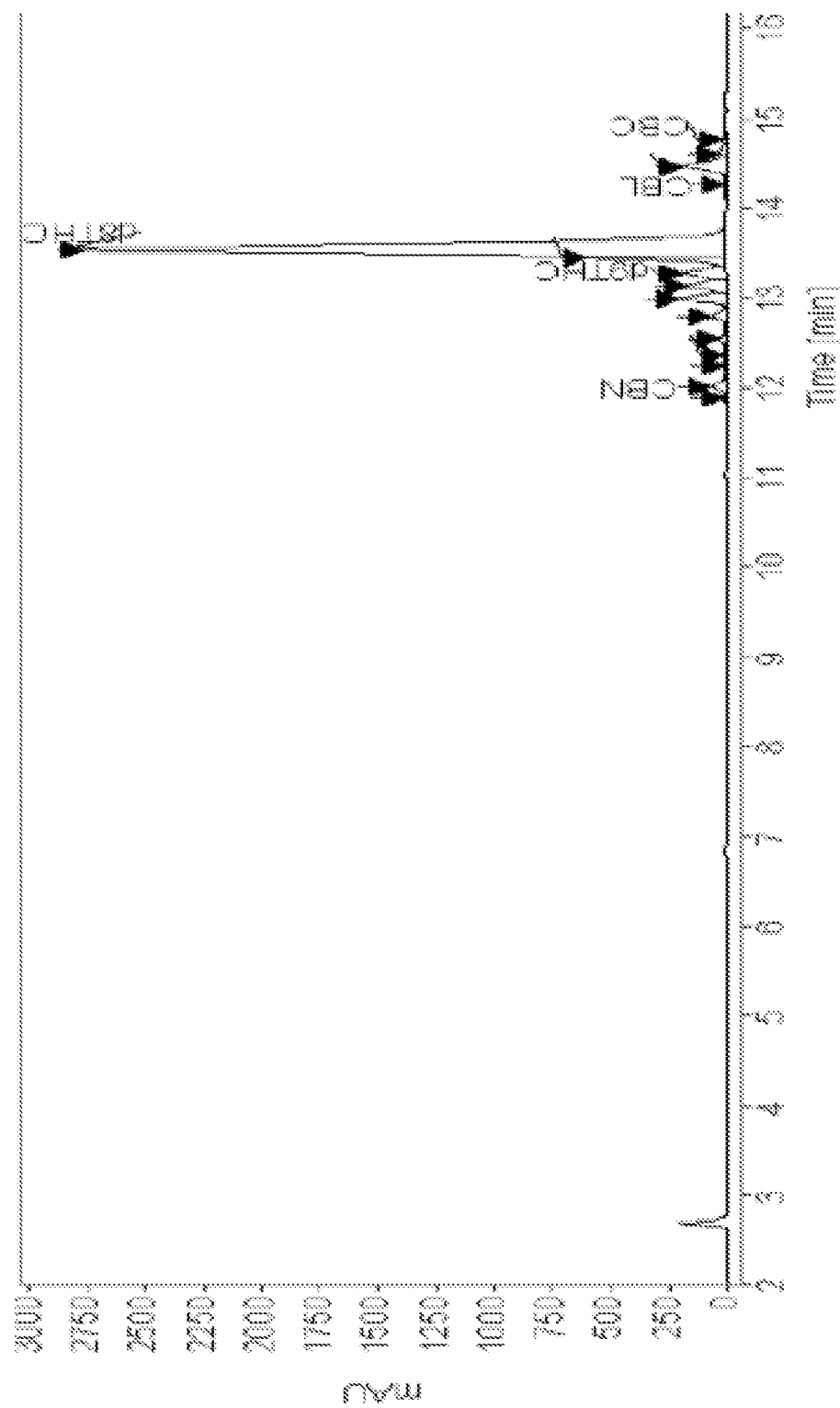
FIG. 2 shows a high-performance liquid chromatogram for EXAMPLE 2.

EXAMPLE 2: To a solution of CBD (500 mg, 1.59 mmol) in heptane (10 mL) was added Al-MCM-41 (1 g, ACS Material). The reaction was stirred at reflux for 18 hours. The reaction was cooled to room temperature and then filtered using a fritted Buchner filtering funnel. The reaction solvent was evaporated in vacuo. Analysis by HPLC showed complete consumption of CBD with $\Delta^8$-THC as the major product (see, TABLE 2 and FIG. 2).

Figure 3:
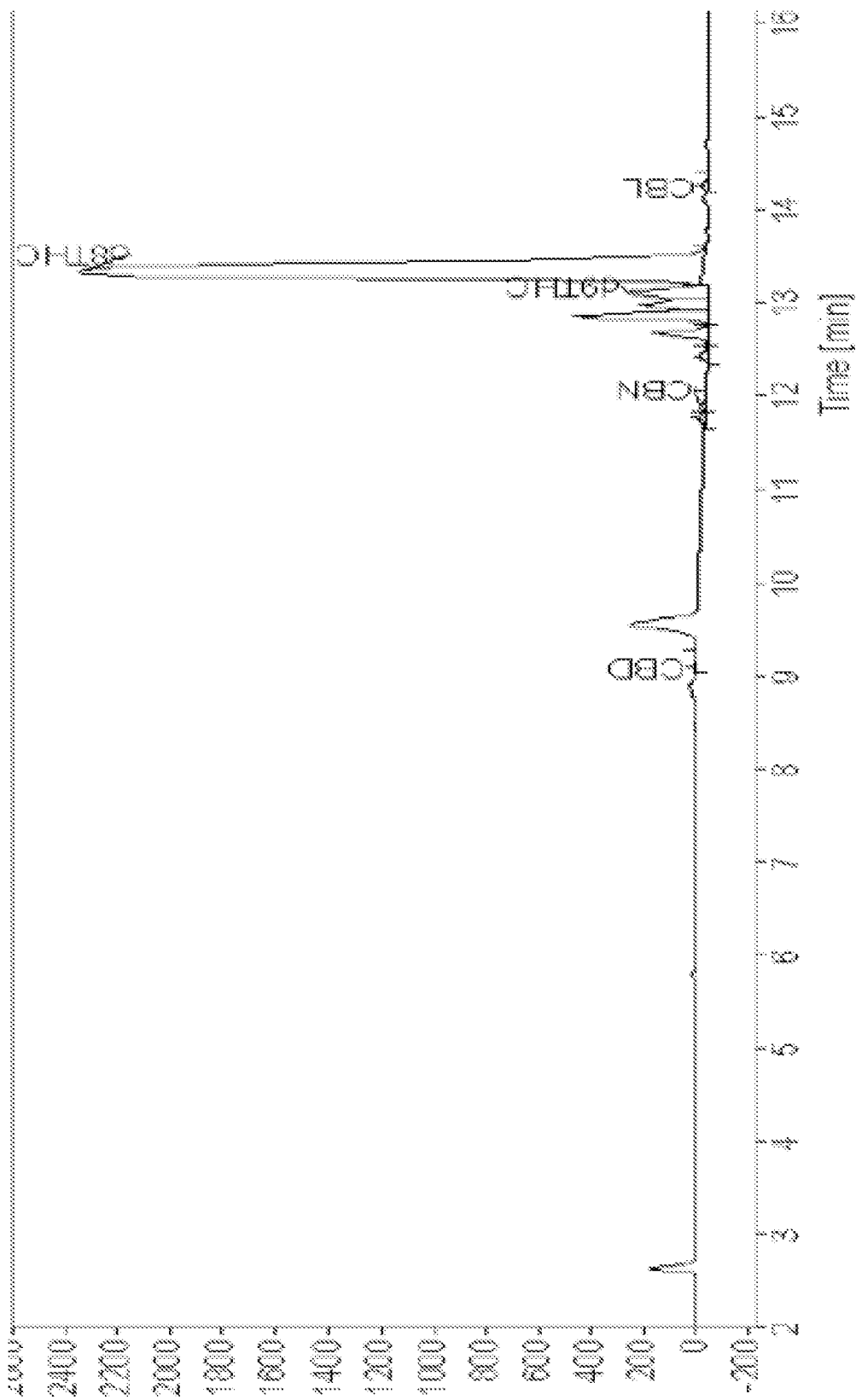
FIG. 3 shows a high-performance liquid chromatogram for EXAMPLE 3.

EXAMPLE 3: To a solution of CBD (500 mg, 1.59 mmol) in heptane (10 mL) was added Amberlyst-15 (500 mg). The reaction was stirred at 60° C. for 2 hours. The reaction was cooled to room temperature and then filtered using a fritted Buchner filtering funnel. The reaction solvent was evaporated in vacuo. Analysis by HPLC showed near complete consumption of CBD (<0.2% remained) with $\Delta^8$-THC as the major product (see, TABLE 2 and FIG. 3).

Figure 4:
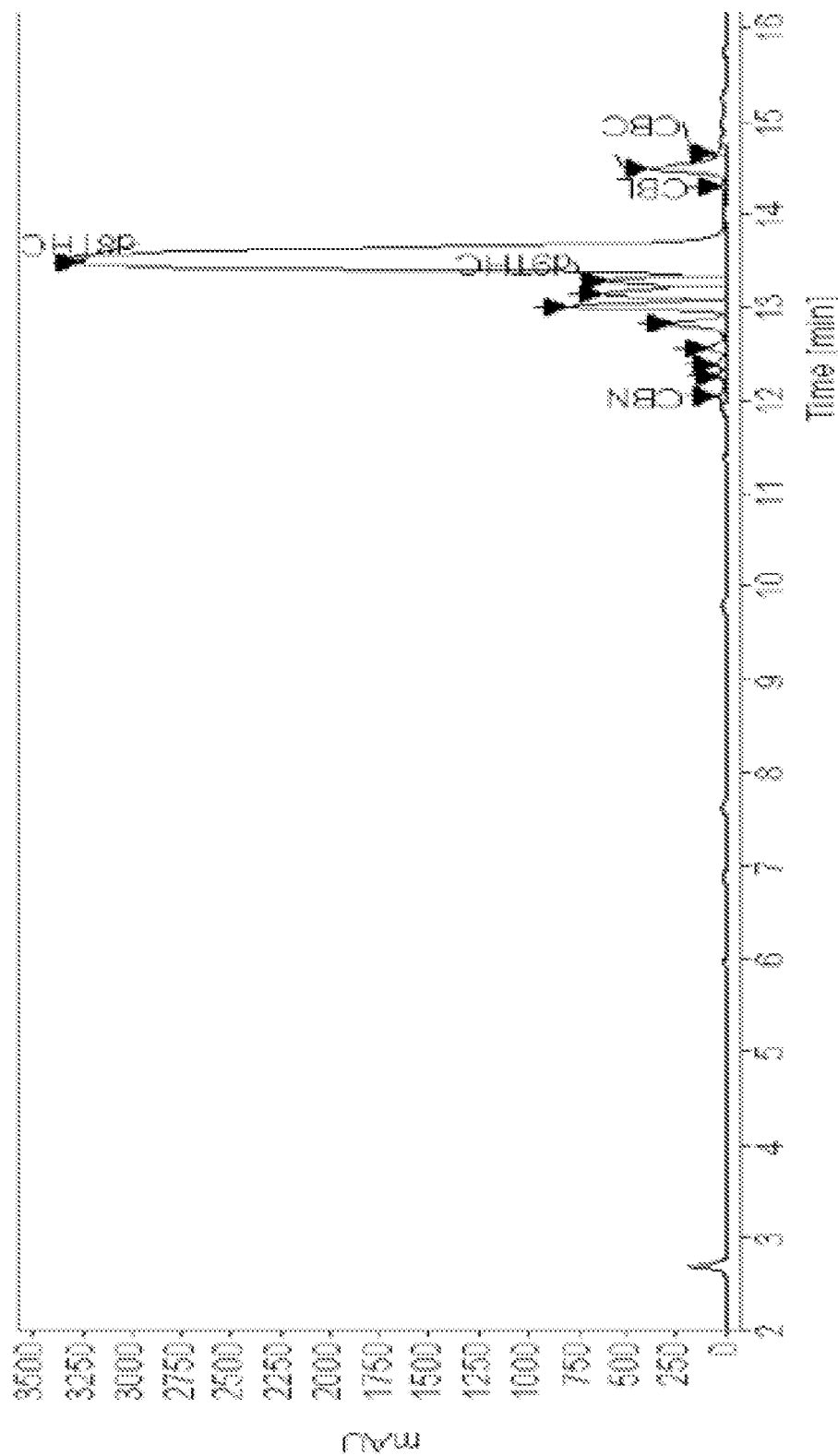
FIG. 4 shows a high-performance liquid chromatogram for EXAMPLE 4.

EXAMPLE 4: To a solution of CBD (500 mg, 1.59 mmol) in heptane (10 mL) was added Amberlyst-15 (500 mg). The reaction was stirred and heated to reflux for 2 hours. The reaction was cooled to room temperature and then filtered using a fritted Buchner filtering funnel. The reaction solvent was evaporated in vacuo. Analysis by HPLC showed complete consumption of CBD with $\Delta^8$-THC as the major product (see, TABLE 2 and FIG. 4).

Figure 5:
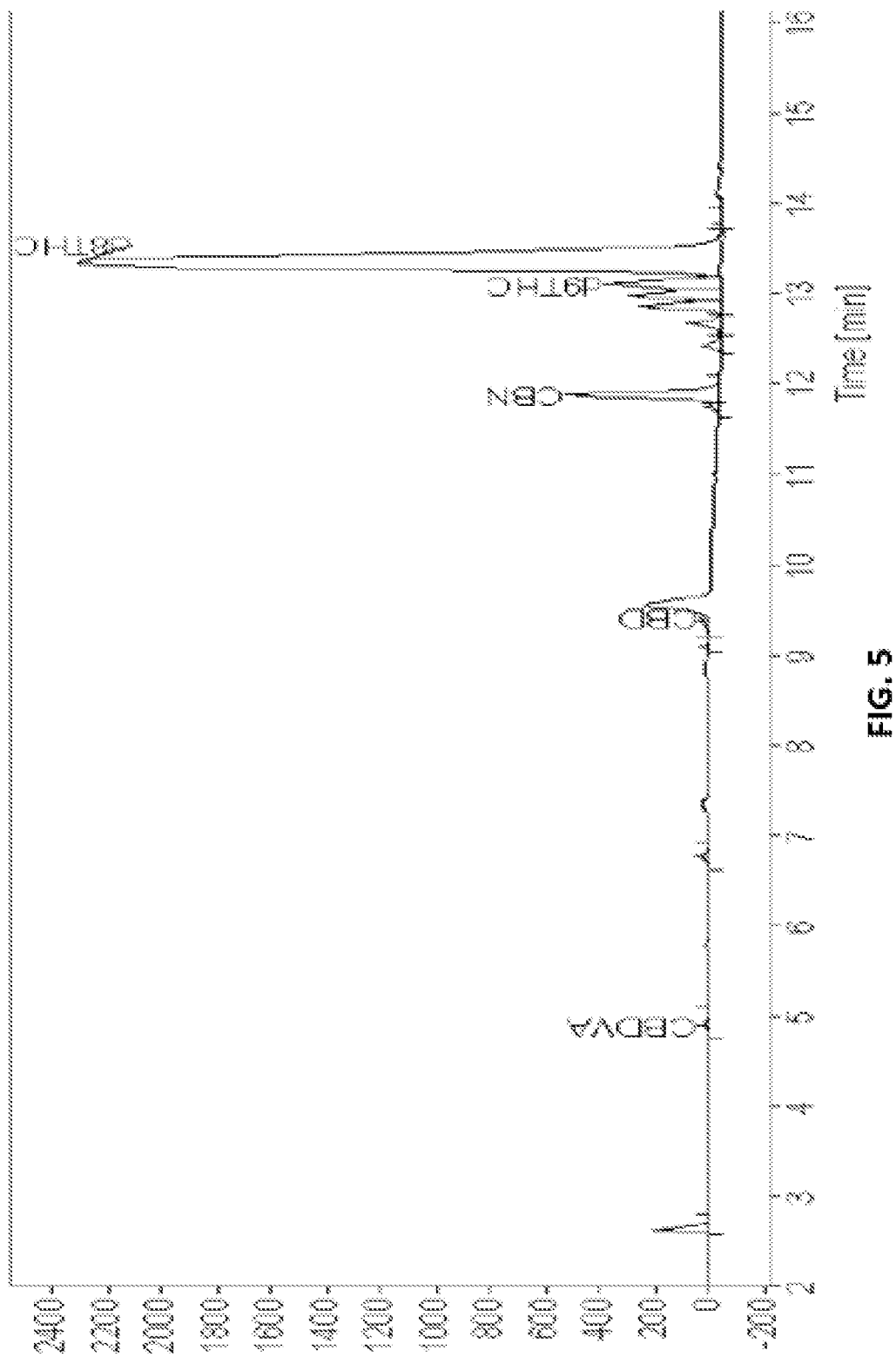
FIG. 5 shows a high-performance liquid chromatogram for EXAMPLE 5.

EXAMPLE 5: A mixture of CBD (500 mg, 1.59 mmol) and ZSM-5 (1 g, ACS Material, P-38, H$^+$) was heated without solvent at 100° C. for 18 hours. The reaction was cooled to room temperature and was diluted with 30 mL of TBME. The resulting suspension was filtered using a fritted Buchner filtering funnel. The solvent from the filtrate was evaporated in vacuo. Analysis by HPLC showed complete consumption of CBD with $\Delta^8$-THC as the major product and $\Delta^9$-THC and cannabinol (CBN) as minor products (see, Table 2 and FIG. 5).

Figure 6:
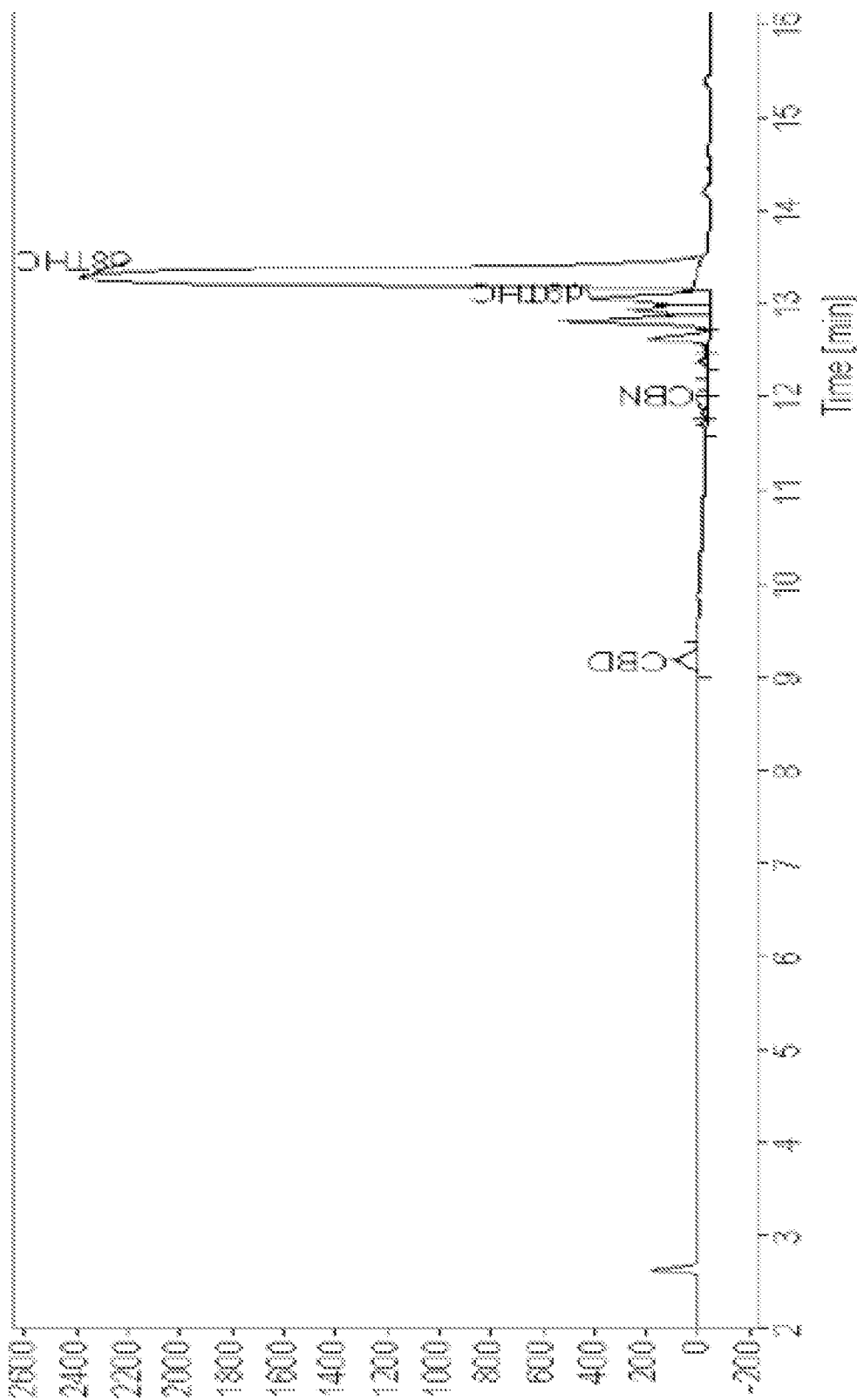
FIG. 6 shows a high-performance liquid chromatogram for EXAMPLE 6.

EXAMPLE 6: To a solution of CBD (500 mg, 1.59 mmol) in heptane (10 mL) was added Amberlyst-15 (500 mg). The reaction was stirred at 80° C. for 2 hours. The reaction was cooled to room temperature and then filtered using a fritted Buchner filtering funnel. The reaction solvent was evaporated in vacuo. Analysis by HPLC showed near complete consumption of CBD (<2% remained) with $\Delta^8$-THC as the major product (see, TABLE 2 and FIG. 6).

Figure 7:
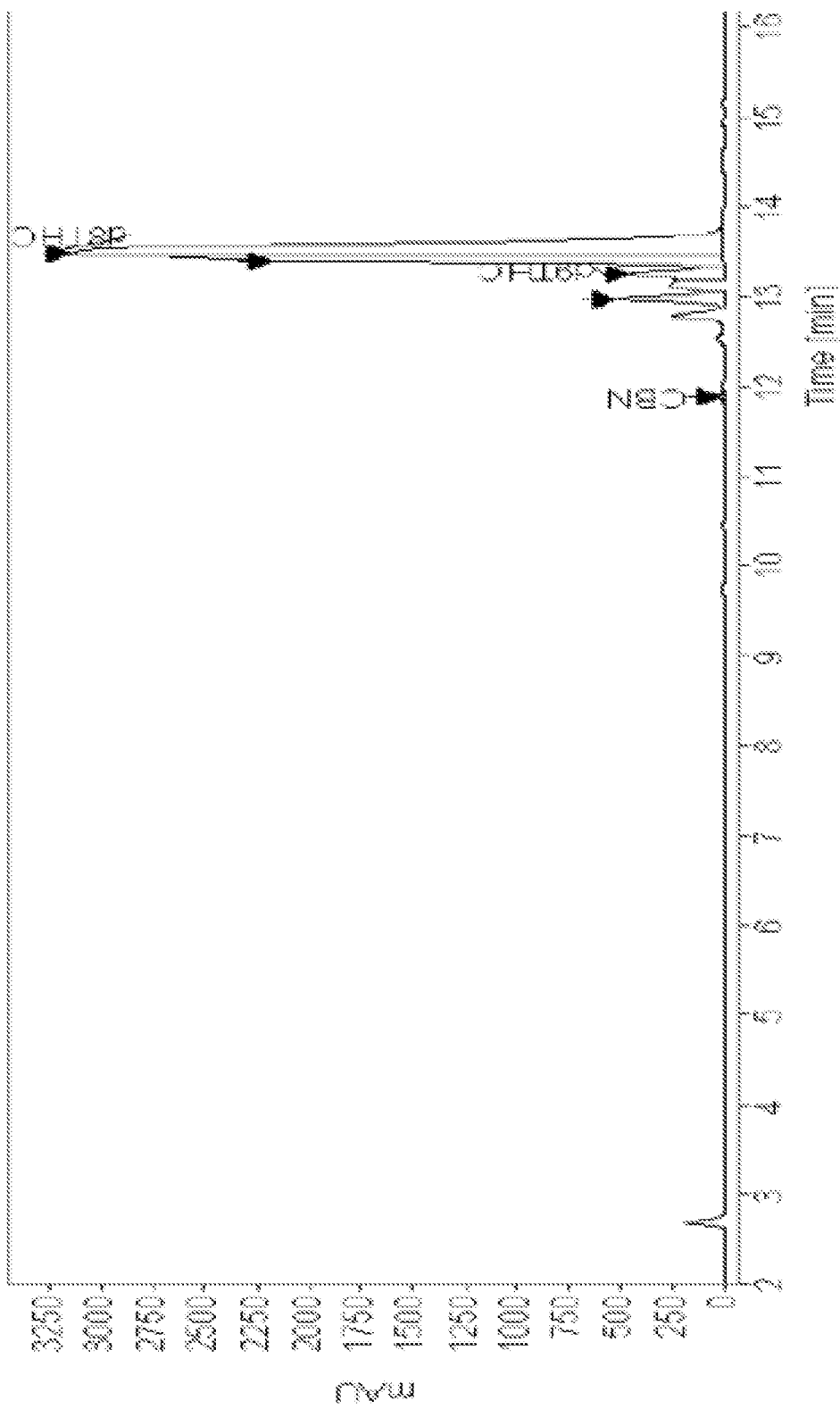
FIG. 7 shows a high-performance liquid chromatogram for EXAMPLE 7.

EXAMPLE 7: To a solution of CBD (500 mg, 1.59 mmol) in heptane (10 mL) was added ZSM-5 (1 g, ACS Material, P-38, Na$^+$). The reaction was stirred at reflux for 18 hours. The reaction was cooled to room temperature and then filtered using a fritted Buchner filtering funnel. The reaction solvent was evaporated in vacuo. Analysis by HPLC showed complete consumption of CBD with $\Delta^8$-THC as the major product (see, TABLE 2 and FIG. 7).

Figure 8:
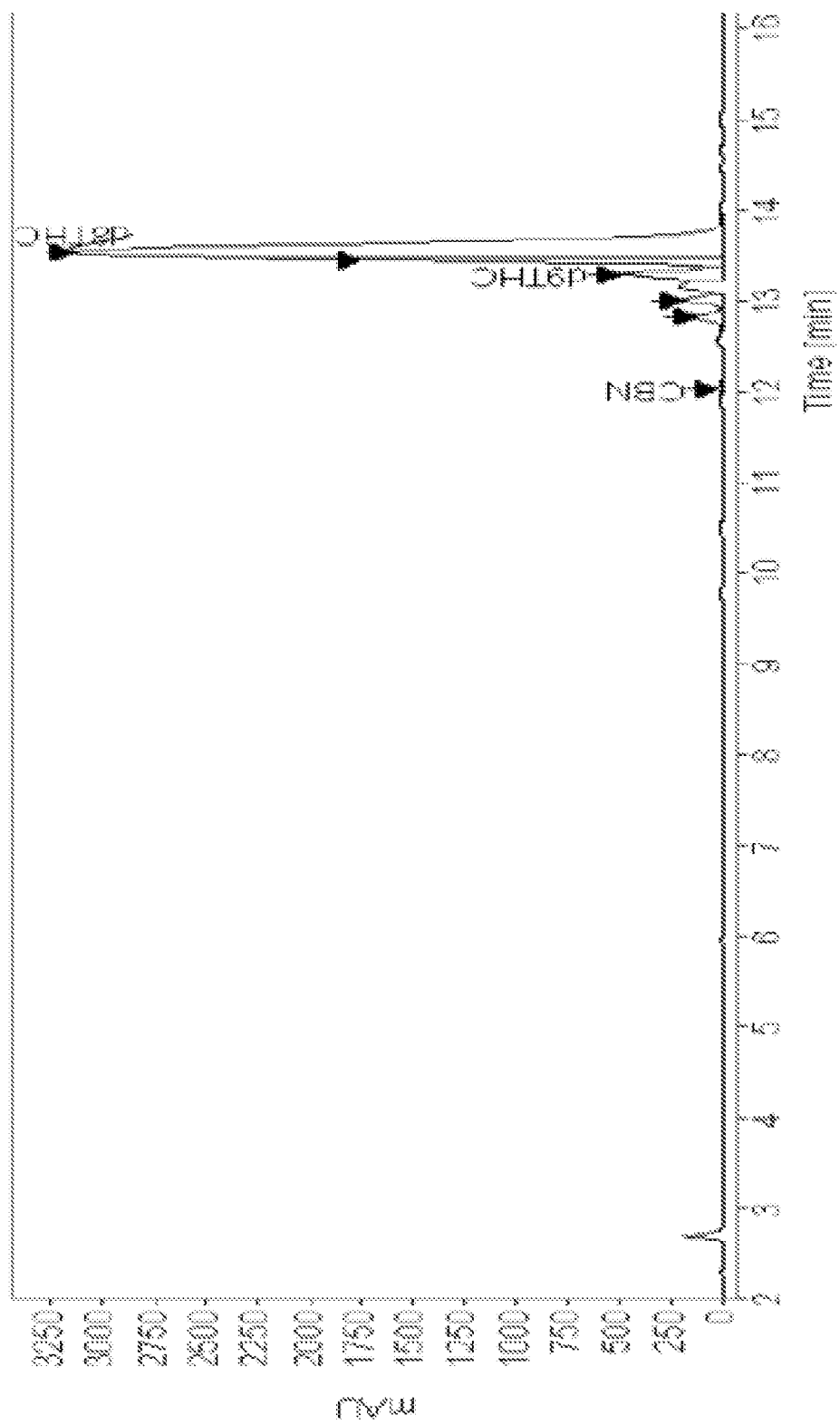
FIG. 8 shows a high-performance liquid chromatogram for EXAMPLE 8.

EXAMPLE 8: To a solution of CBD (500 mg, 1.59 mmol) in heptane (10 mL) was added ZSM-5 (1 g, ACS Material, P-38, H$^+$). The reaction was stirred at reflux for 2 hours. The reaction was cooled to room temperature and then filtered using a fritted Buchner filtering funnel. The reaction solvent was evaporated in vacuo. Analysis by HPLC showed complete consumption of CBD with $\Delta^8$-THC as the major products (see, TABLE 2 and FIG. 8).

Figure 9:
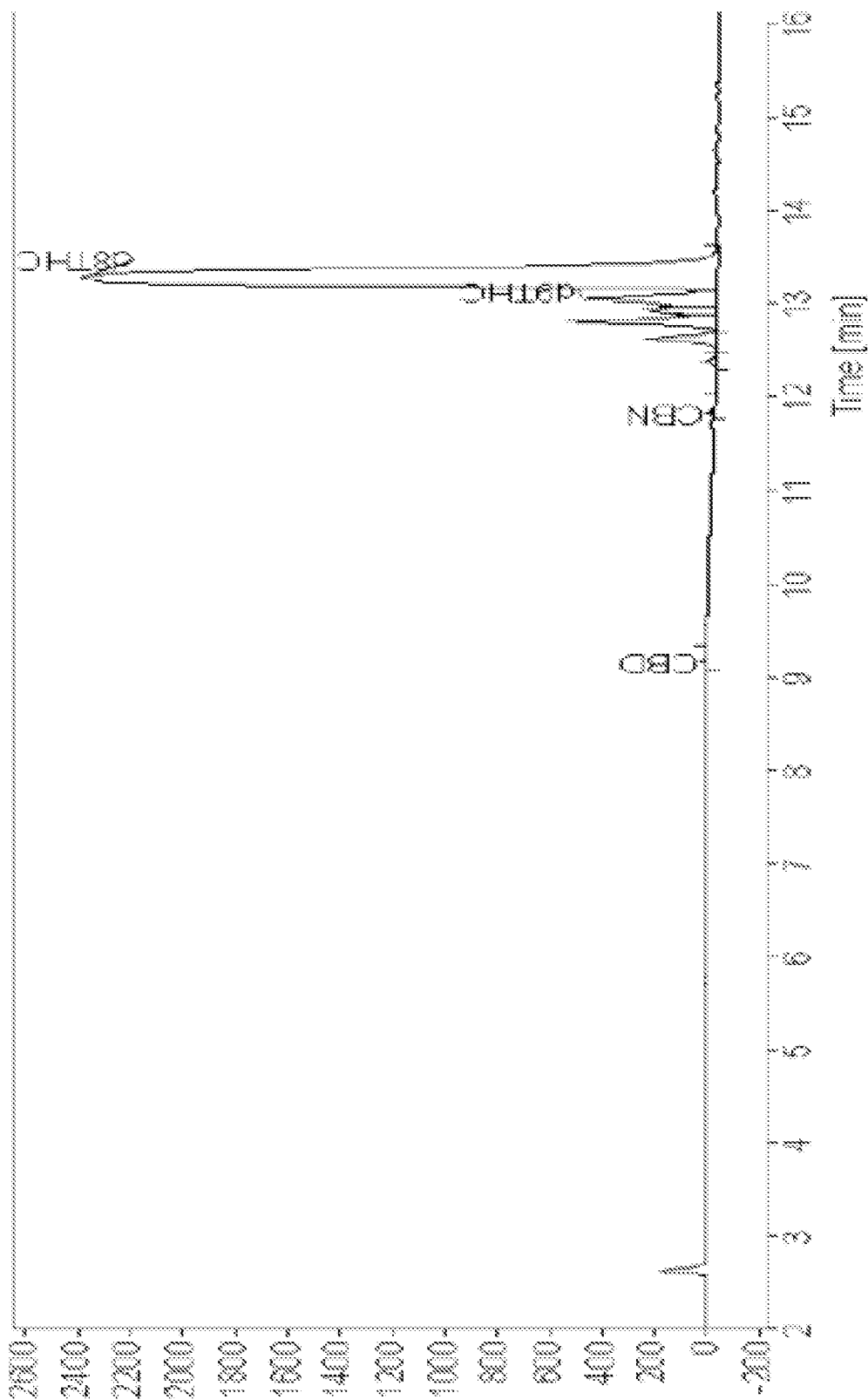
FIG. 9 shows a high-performance liquid chromatogram for EXAMPLE 9.

EXAMPLE 9: To a solution of CBD (500 mg, 1.59 mmol) in heptane (10 mL) was added ZSM-5 (1 g, ACS Material, P-38, H$^+$). The reaction was stirred at reflux for 18 hours. The reaction was cooled to room temperature and was filtered using a fritted Buchner filtering funnel. The reaction solvent was evaporated in vacuo. Analysis by HPLC showed complete consumption of CBD with $\Delta^8$-THC as the major product (see, TABLE 2 and FIG. 9).

Figure 10:
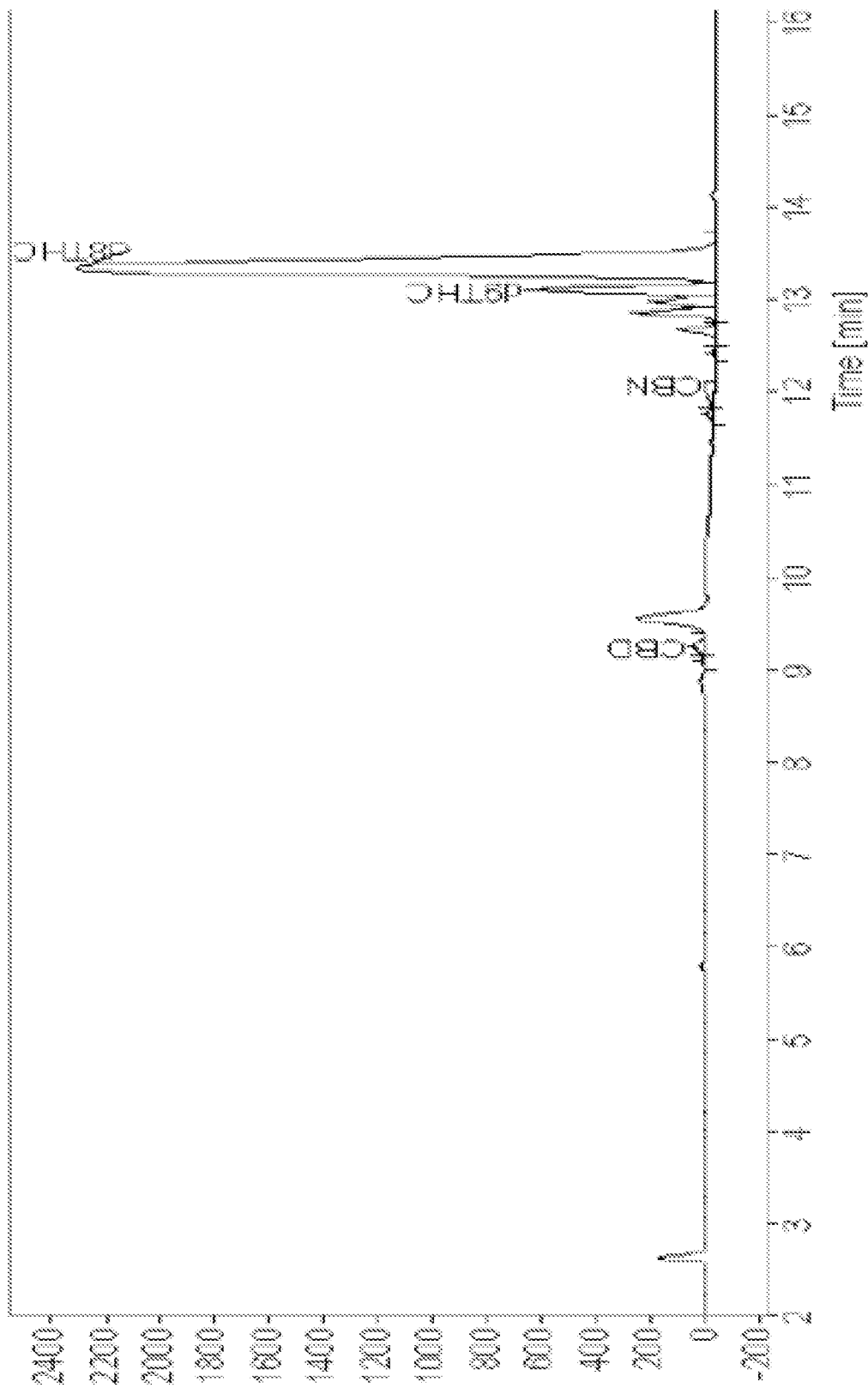
FIG. 10 shows a high-performance liquid chromatogram for EXAMPLE 10.

EXAMPLE 10: To a solution of CBD (500 mg, 1.59 mmol) in heptane (10 mL) was added Amberlyst-15 (500 mg). The reaction was stirred at room temperature for 2 hours. The reaction was filtered using a fritted Buchner filtering funnel, and then the reaction solvent was evaporated in vacuo. Analysis by HPLC showed near complete consumption of CBD (<1% remained) with $\Delta^8$-THC as the major product and $\Delta^9$-THC as a minor product (see, TABLE 2 and FIG. 10).

Figure 11:
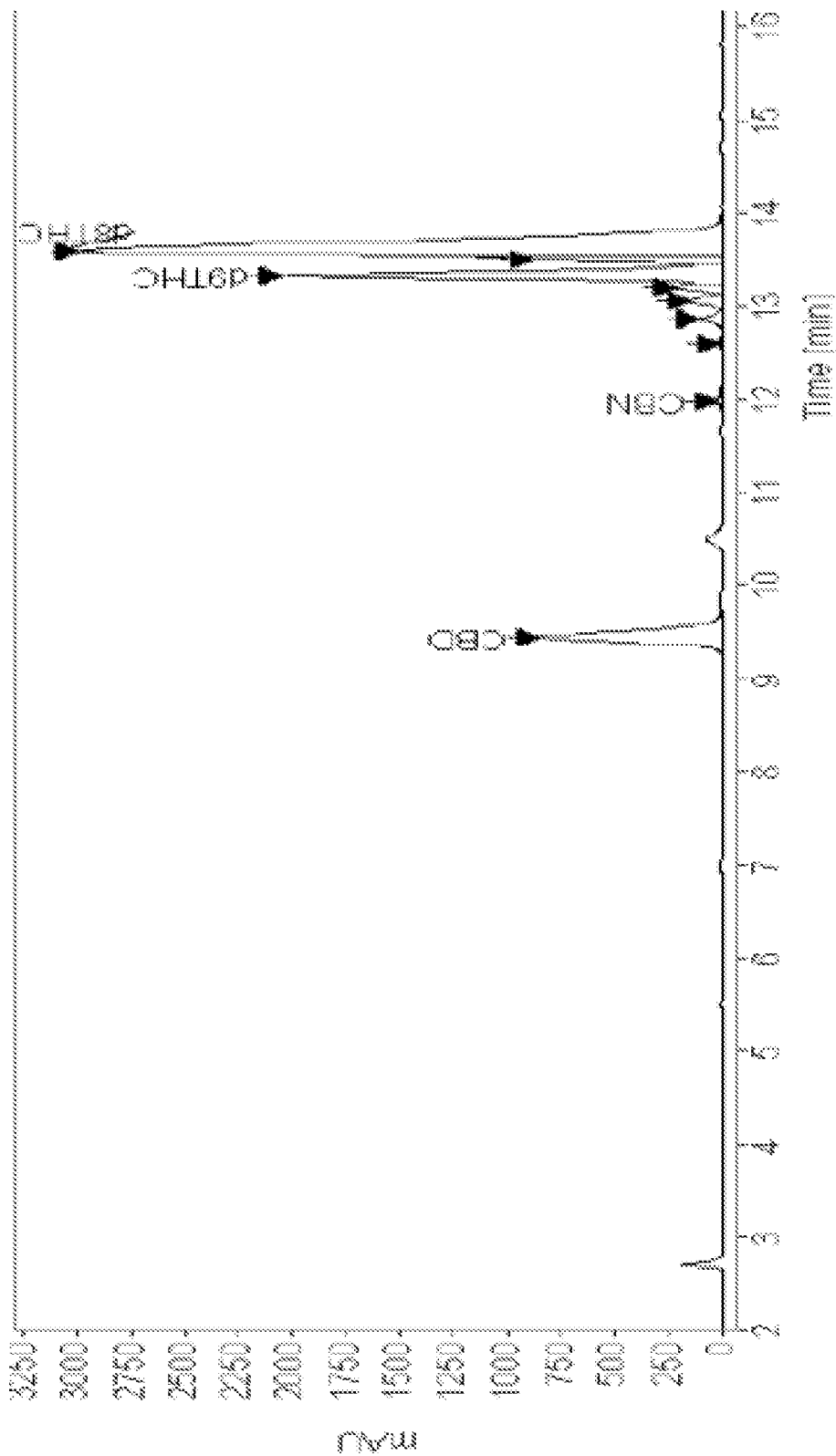
FIG. 11 shows a high-performance liquid chromatogram for EXAMPLE 11.

EXAMPLE 11: To a solution of cannabidiol (500 mg, 1.59 mmol) in heptane (10 mL) was added Amberlyst-15 (50 mg). The reaction was stirred at room temperature for 24 hours. The reaction was filtered using a fritted Buchner filtering funnel and the reaction solvent was evaporated in vacuo. Analysis by HPLC showed unreacted CBD (<12% remained) with $\Delta^8$-THC as the major product and $\Delta^9$-THC as a minor product (see, TABLE 2 and FIG. 11).

Figure 12:
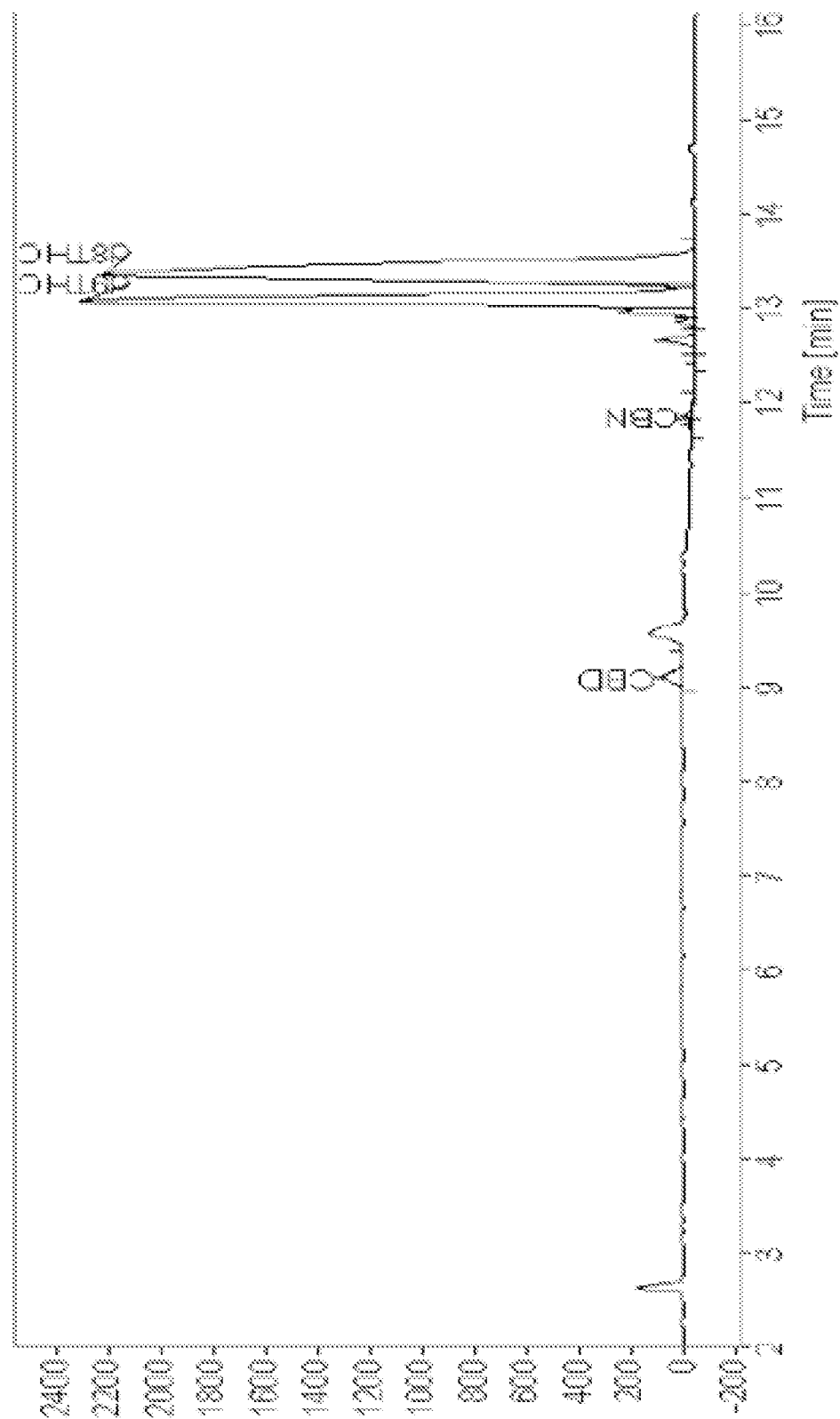
FIG. 12 shows a high-performance liquid chromatogram for EXAMPLE 12.

EXAMPLE 12: To a solution of CBD (500 mg, 1.59 mmol) in heptane (10 mL) was added ZSM-5 (1 g, ACS Material, P-38, H$^f$). The reaction was stirred at 80° C. for 18 hours. The reaction was cooled to room temperature and then filtered using a fritted Buchner filtering funnel. The reaction solvent was evaporated in vacuo. Analysis by HPLC showed near complete consumption of CBD (<2% remained) with a mixture of $\Delta^8$-THC $\Delta^9$-THC as the major products (see, TABLE 2 and FIG. 12).

TABLE 2

HPLC results from EXAMPLES 1-12. Percentage values for CBD, $\Delta^8$-THC and $\Delta^9$-THC were determined by HPLC-DAD (215 nm).

| Example | CBD (%) | $\Delta^9$-THC (%) | $\Delta^8$-THC (%) | $\Delta^8$-THC:$\Delta^9$-THC |
|---|---|---|---|---|
| 1 | 0.6 | 3.3 | 68.5 | 20.8:1.0 |
| 2 | 0 | 3.9 | 73.8 | 18.9:1.0 |
| 3 | 0.1 | 5.3 | 81.1 | 15.3:1.0 |
| 4 | 0 | 5.1 | 74.0 | 14.7:1.0 |
| 5 | 0.2 | 6.0 | 77.0 | 12.3:1.0 |
| 6 | 1.9 | 6.6 | 77.0 | 11.7:1.0 |
| 7 | 0 | 5.8 | 71.5 | 11.2:1.0 |
| 8 | 0.0 | 6.5 | 71.5 | 11.0:1.0 |
| 9 | 0 | 7.6 | 79.0 | 10.4:1.0 |
| 10 | 0.7 | 9.7 | 80.4 | 8.3:1.0 |
| 11 | 13.9 | 21.2 | 54.9 | 2.6:1.0 |
| 12 | 1.5 | 36.3 | 55.2 | 1.5:1.0 |

Figure 13:
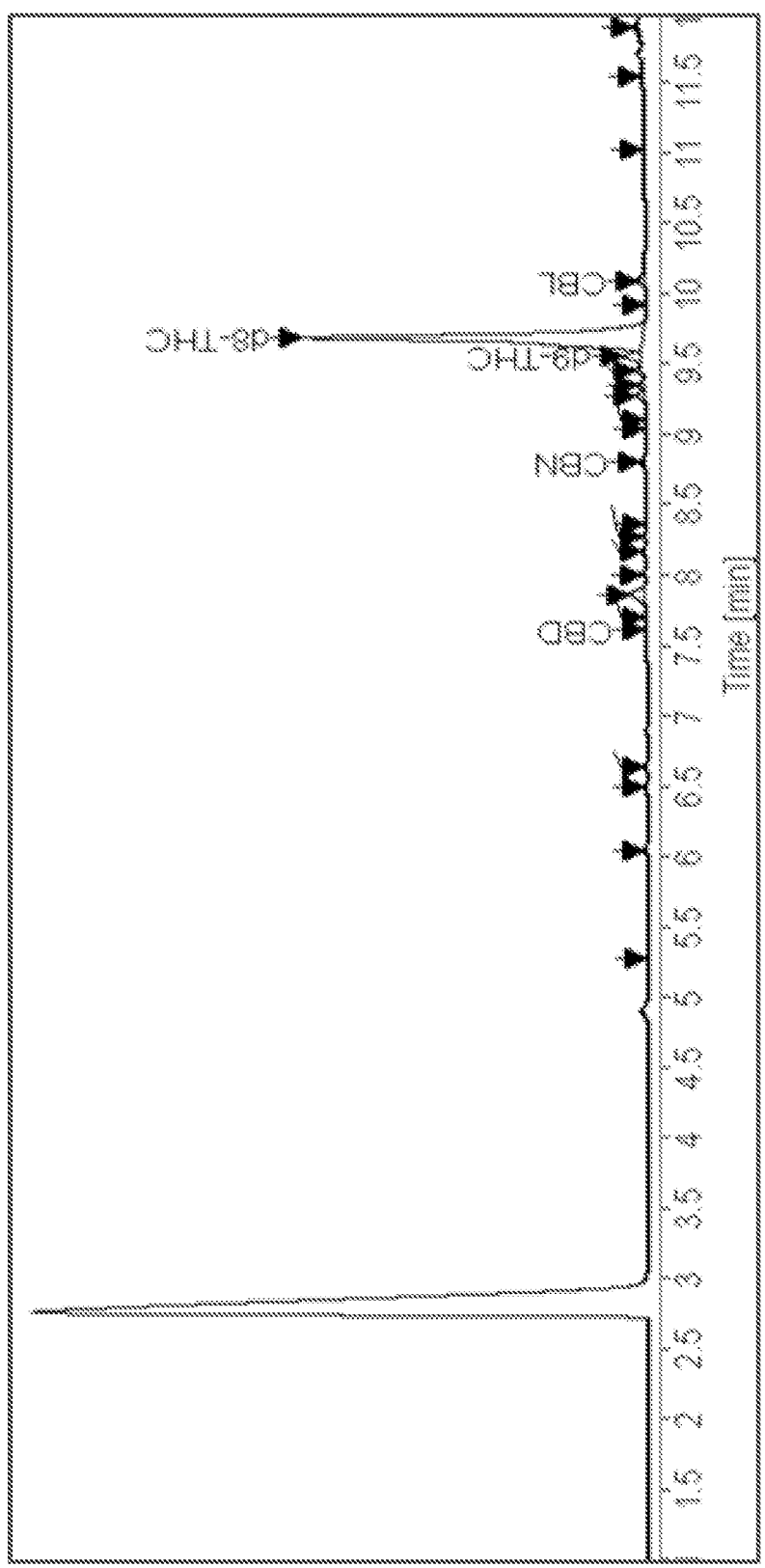
FIG. 13 shows a high-performance liquid chromatogram for EXAMPLE 13.

EXAMPLE 13: To a solution of CBD distillate (1.030 g) in heptane (20 mL) was added Al-MCM-41 (1.004 g). The reaction was stirred at 65° C. for 24 hours. The supernatant was concentrated using rotary evaporator and then filtered. The resultant solution was evaporated to dryness using centrifuge evaporator. Analysis by HPLC showed near complete conversion (<1% remaining) with the major product being $\Delta^8$-THC (see Table 3 and FIG. 13).

TABLE 3

HPLC results from EXAMPLE 13. Percentage values for CBD, $\Delta^8$-THC and $\Delta^9$-THC were determined by HPLC-DAD (215 nm).

| | Original distillate | Al-MCM-41 at 65 C. |
|---|---|---|
| CBD w/w % | 68.35 | 0.24 |
| $\Delta^9$-THC w/w % | 2.34 | 2.46 |
| $\Delta^8$-THC w/w % | 0.04 | 68.71 |
| CBN w/w % | 0.38 | 1.04 |
| CBDV w/w % | 3.57 | 0 |
| CBC w/w % | 4.05 | 0 |
| CBL w/w % | 0.52 | 1.17 |
| CBT w/w % | 0.52 | 0.82 |
| Total cannabinoids | ~78% | ~75% |

EXAMPLE 14: Under heated conditions, CBD isolate and a molar excess of acidic alumina were reacted within a rotating bed reactor. Heptane was used as a solvent to dissolve the CBD isolate and solid acidic alumina was within the reactor bed. The conversion of CBD to predominantly $\Delta$8-THC is shown in Table 4 under different conditions.

TABLE 4

Weight percent values for CBD, Δ⁸-THC and Δ⁹-THC in the resulting reaction mixture

| Trial | Rotary Bed Reactor (RPM) | Jacket Heater Temp (° C.) | Time (hours) | Reaction Mixture | | |
|---|---|---|---|---|---|---|
| | | | | CBD (% w/w) | Δ9-THC (% w/w) | Δ8-THC (% w/w) |
| 1 | 500 | 102 | 27.5 | 0.39 | 6.18 | 67.31 |
| 2 | 500 | 102 | 29 | 0.95 | 8.82 | 70.55 |
| 3 | 750 | 102 | 24 | 1.34 | 5.04 | 76.23 |
| 4 | 250 | 102 | 31 | 3.69 | 4.96 | 77.45 |
| 5* | 500 | 104 | 6.5 | <LOD | 3.48 | 79.54 |
| 6 | 500 | 104 | 24 | 0.01 | 3.66 | 87.11 |

*System purged with N₂
LOD = Limit of Detection

The reactions provide high conversion outcomes to predominantly Δ8-THC, with the use of inert atmosphere (e.g. nitrogen) accelerating the conversion to Δ8-THC.

EXAMPLE 15: To a solution of CBDV in heptane was added a molar excess of acidic alumina. The reaction was stirred under heated conditions for a period of time to form Δ⁸-THCV. The supernatant was concentrated using rotary evaporator and then filtered. The resultant solution was evaporated to dryness using centrifuge evaporator. Analysis by HPLC showed partial conversion to Δ⁸-THCV.

EXAMPLE 16: To a solution of CBDV in heptane (with a co-solvent such as ethyl acetate, TBME, and acetone) is added a molar excess of acidic alumina. The reaction is stirred under heated conditions for a period of time to form Δ⁸-THCV. The supernatant is concentrated using rotary evaporator and then filtered. The resultant solution is evaporated to dryness using centrifuge evaporator.

EXAMPLE 17: To a solution of CBDP in heptane is added a molar excess of acidic alumina. The reaction is stirred under heated conditions for a period of time to form Δ⁸-THCP. The supernatant is concentrated using rotary evaporator and then filtered. The resultant solution is evaporated to dryness using centrifuge evaporator.

EXAMPLE 18: To a solution of CBDA in heptane (with a co-solvent such as ethyl acetate, TBME, and acetone) is added a molar excess of acidic alumina. The reaction is stirred under heated conditions in an inert atmosphere (e.g. N₂) for a period of time to form Δ⁸-THCA. The supernatant is concentrated using rotary evaporator and then filtered. The resultant solution is evaporated to dryness using centrifuge evaporator.

In the present disclosure, all terms referred to in singular form are meant to encompass plural forms of the same. Likewise, all terms referred to in plural form are meant to encompass singular forms of the same. Unless defined otherwise, all technical and scientific terms used herein have the same meaning as commonly understood by one of ordinary skill in the art to which this disclosure pertains.

As used herein, the term "about" refers to an approximately +/−10% variation from a given value. It is to be understood that such a variation is always included in any given value provided herein, whether or not it is specifically referred to.

It should be understood that the compositions and methods are described in terms of "comprising," "containing," or "including" various components or steps, the compositions and methods can also "consist essentially of" or "consist of" the various components and steps. Moreover, the indefinite articles "a" or "an," as used in the claims, are defined herein to mean one or more than one of the element that it introduces.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values even if not explicitly recited. Thus, every point or individual value may serve as its own lower or upper limit combined with any other point or individual value or any other lower or upper limit, to recite a range not explicitly recited.

Therefore, the present disclosure is well adapted to attain the ends and advantages mentioned as well as those that are inherent therein. The particular embodiments disclosed above are illustrative only, as the present disclosure may be modified and practiced in different but equivalent manners apparent to those skilled in the art having the benefit of the teachings herein. Although individual embodiments are discussed, the disclosure covers all combinations of all those embodiments. Furthermore, no limitations are intended to the details of construction or design herein shown, other than as described in the claims below. Also, the terms in the claims have their plain, ordinary meaning unless otherwise explicitly and clearly defined by the patentee. It is therefore evident that the particular illustrative embodiments disclosed above may be altered or modified and all such variations are considered within the scope and spirit of the present disclosure. If there is any conflict in the usages of a word or term in this specification and one or more patent(s) or other documents that may be incorporated herein by reference, the definitions that are consistent with this specification should be adopted.

Many obvious variations of the embodiments set out herein will suggest themselves to those skilled in the art in light of the present disclosure. Such obvious variations are within the full intended scope of the appended claims.

The invention claimed is:

1. A method for converting a compound of Formula (I) into a compound of Formula (II), the method comprising heating a compound of Formula (I)

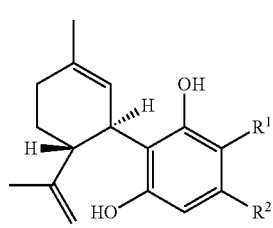

(I)

and a Lewis-acidic heterogeneous reagent in an aprotic-solvent system, to provide a compound of Formula (II)

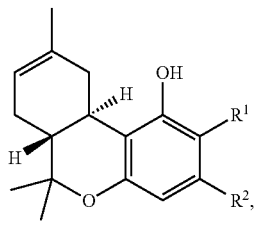

(II)

wherein the Lewis-acidic heterogeneous reagent is acidic alumina, and
wherein:
$R^1$ is hydrogen or COOH, and
$R^2$ is hydrogen, $C_1$-$C_{12}$ alkyl, $C_2$-$C_{12}$ alkenyl, $C_2$-$C_{12}$ alkynyl, $(OCH_2CH_2)_{0-6}O(C_1$-$C_8$ alkyl), $(C_0$-$C_4$ alkyl)-$NR^{2a}R^{2b}$, $(C_0$-$C_4$ alkyl)-aryl, $(C_0$-$C_4$ alkyl)-heteroaryl, $(C_0$-$C_4$ alkyl)-cycloalkyl, or $(C_0$-$C_4$ alkyl)-heterocycloalkyl, wherein $R^{2a}$ and $R^{2b}$ are each independently hydrogen or $C_1$-$C_6$ alkyl.

2. The method of claim 1, wherein the heating step occurs at a temperature in a range from about 80° C. to about 110° C.

3. The method of claim 1, wherein the heating step occurs at a temperature in a range from about 80° C. to about 100° C.

4. The method of claim 1, wherein the heating step occurs at a temperature in a range from about 80° C. to about 95° C.

5. The method of claim 1, wherein the heating step occurs in an inert atmosphere.

6. The method of claim 1, wherein the heating step is performed in a stirred tank reactor or a rotary bed reactor.

7. The method of claim 1, wherein the Lewis-acidic heterogeneous reagent is in an amount of between about 0.1 to about 100 molar equivalents with respect to the compound of Formula (I).

8. The method of claim 1, wherein the Lewis-acidic heterogeneous reagent is in an amount of between about 1 to about 50 molar equivalents with respect to the compound of Formula (I).

9. The method of claim 1, wherein the Lewis-acidic heterogeneous reagent is in an amount of between about 1 to about 25 molar equivalents with respect to the compound of Formula (I).

10. The method of claim 1, wherein the Lewis-acidic heterogeneous reagent is in an amount of between about 1 to about 10 molar equivalents with respect to the compound of Formula (I).

11. The method of claim 1, wherein the Lewis-acidic heterogeneous reagent is in an amount of between about 1 to about 5 molar equivalents with respect to the compound of Formula (I).

12. The method of claim 1, wherein the aprotic-solvent system comprises acetone, dimethyl sulfoxide, ethyl acetate, dichloromethane, chloroform, toluene, pentane, heptane, hexane, diethyl ether, tert-butyl methyl ether, tetrahydrofuran, dioxane, dimethylformamide, dimethylacetamide, N-methylpyrrolidone, anisole, butyl acetate, cumene, ethyl formate, isobutyl acetate, isopropyl acetate, methyl acetate, methylethylketone, methylisobutylketone, propyl acetate, cyclohexane, para-xylene, meta-xylene, ortho-xylene, or 1,2-dichloroethane, or any combination thereof.

13. The method of claim 1, wherein the aprotic-solvent system is heptane.

14. The method of claim 1, further comprising drying the acidic alumina before the heating step.

15. The method of claim 1, wherein $R^1$ is hydrogen.

16. The method of claim 1, wherein $R^2$ is $C_3H_7$, $C_5H_{11}$ or $C_7H_{15}$.

17. The method of claim 1, wherein the compound of Formula (I) is cannabidiol (CBD) and the compound of Formula (II) is $\Delta^8$-tetrahydrocannabinol ($\Delta^8$-THC).

18. A method for converting cannabidiol (CBD) into $\Delta^8$-tetrahydrocannabinol ($\Delta^8$-THC), the method comprising heating CBD and a Lewis-acidic heterogeneous reagent in an aprotic-solvent system at a temperature in a range from about 80° C. to about 110° C., and wherein the Lewis-acidic heterogeneous reagent is acidic alumina and is in an amount of between about 1 to about 100 molar equivalents with respect to CBD.

19. The method of claim 18, wherein the aprotic-solvent system comprises acetone, dimethyl sulfoxide, ethyl acetate, dichloromethane, chloroform, toluene, pentane, heptane, hexane, diethyl ether, tert-butyl methyl ether, tetrahydrofuran, dioxane, dimethylformamide, dimethylacetamide, N-methylpyrrolidone, anisole, butyl acetate, cumene, ethyl formate, isobutyl acetate, isopropyl acetate, methyl acetate, methylethylketone, methylisobutylketone, propyl acetate, cyclohexane, para-xylene, meta-xylene, ortho-xylene, or 1,2-dichloroethane, or any combination thereof.

20. The method of claim 18, wherein the aprotic-solvent system is heptane.

\* \* \* \* \*